United States Patent [19]

Gottstein et al.

[11] 4,100,346

[45] Jul. 11, 1978

[54] CERTAIN 7(O-AMINO-METHYL- OR METHYLAMINOMETHYLPHENYL- OR CYCLOHEXADIENYL- OR THIENYLACETAMIDE)-3[1-CARBOXYMETHYL-(OR ETHYL- OR PROPYL-)-TETRAZOL-5-YLTHIOMETHYL]-3-CEPHEM-4-CARBOXYLIC ACIDS

[75] Inventors: William J. Gottstein, Fayetteville; Murray A. Kaplan, Syracuse; Alphonse P. Granatek, Baldwinsville, all of N.Y.

[73] Assignee: Bristol-Myers Company, New York, N.Y.

[21] Appl. No.: 695,231

[22] Filed: Jun. 11, 1976

Related U.S. Application Data

[63] Continuation-in-part of Ser. No. 590,971, Jun. 27, 1975, which is a continuation-in-part of Ser. No. 502,991, Sep. 3, 1974, abandoned.

[51] Int. Cl.$^2$ .................. C07D 501/36; A61K 31/545
[52] U.S. Cl. ........................................ 544/27; 544/26; 424/246
[58] Field of Search ................ 260/243 C; 544/26, 27

[56] References Cited

U.S. PATENT DOCUMENTS 3,819,623  6/1974  Takano et al. .................... 260/243 C Primary Examiner—Nicholas S. Rizzo
Attorney, Agent, or Firm—Herbert W. Taylor, Jr.

[57] ABSTRACT

Certain 7-acylamido-3-[1-carboxymethyl-(or ethyl- or propyl-)-tetrazol-5-ylthiomethyl]-3-cephem-4-carboxylic acids and their salts and easily hydrolyzed esters of the 4-carboxyl group were synthesized and found to be potent antibacterial agents which exhibited good aqueous solubility. A preferred embodiment was 7-(2-aminomethylphenylacetamido)-3-(1-carboxymethyltetrazol-5-ylthiomethyl)-3-cephem-4-carboxylic acid.

17 Claims, No Drawings

CERTAIN 7(O-AMINO-METHYL- OR METHYLAMINOMETHYLPHENYL- OR CYCLOHEXADIENYL- OR THIENYLACETAMIDE)-3[1-CARBOXYMETHYL- (OR ETHYL- OR PROPYL-)-TETRAZOL-5-YLTHIOMETHYL]-3-CEPHEM-4-CARBOXYLIC ACIDS

CROSS-REFERENCE TO RELATED APPLICATIONS

This application is a continuation-in-part of our prior, copending application Ser. No. 590,971 filed June 27, 1975 which was in turn a copending continuation-in-part of our prior application Ser. No. 502,991 filed Sept. 3, 1974 and now abandoned.

BACKGROUND OF THE INVENTION

1. Field of the Invention

The cephalosporins of the present invention in general possess the usual attributes of such compounds and are particularly useful in the treatment of bacterial infections.

2. Description of the Prior Art

The cephalosporins are a well-known group of semi-synthetic antibacterial agents made originally, for example, by acylation of the 7-amino group of the nucleus 7-aminocephalosporanic acid (7-ACA) and later by similar acylation of nuclei derived therefrom, as by modification of its substituent at the 3-position. Various reviews have appeared in the scientific literature (e.g. Cephalosporins and Penicillins - Chemistry and Biology, edited by Edwin H. Flynn, Academic Press, New York, 1972, and particularly pages 554–569) and in the patent literature, e.g. as in U.S. Pat. Nos. 3,687,948; 3,741,965; 3,743,644; 3,759,904; 3,759,905; 3,766,175; 3,766,906; 3,769,281; 3,796,801; 3,799,923; 3,812,116; 3,813,388; 3,814,754 and 3,814,755 (all U.S. Class 260–243C).

Issued patents on 3-thiolated cephalosporins in which the 7-substituent is (a) α-Amino-α-phenylacetamido include U.S. Pat. Nos. 3,641,021, 3,734,907, 3,687,948, 3,741,965, 3,757,015, 3,743,644, Japan Pat. No. 71/24400 (Farmdoc 46374S), Belgium Pat. No. 776,222 (Farmdoc 38983T; U.K. Pat. No. 1,328,340 which includes various substituents on the benzene ring), Belgium Pat. No. 772,592 (Farmdoc 19696T; U.S. Pat. Nos. 3,687,948, 3,734,907 and 3,757,012), West Germany Pat. No. 2,202,274 (Farmdoc 50428T) corresponding to U.S. Pat. No. 3,759,904, Netherlands 7205644 (Farmdoc 76309T; U.S. Pat. No. 3,757,014); and (b) o-, m- or p-aminoethoxyphenylacetamido as Netherlands Pat. No. 72/13968 (Farmdoc 24740U) corresponding to U.S. Pat. No. 3,759,905 and (c) o-aminomethylphenylacetamido particularly as reviewed in U.S. Pat. No. 3,823,141 and also as Netherlands Pat. No. 72/06326 (Farmdoc 76374T) (which also reviews the older patent literature concerning substituted 7-phenylacetamidocephalosporanic acids) corresponding to U.S. Pat. Nos. 3,766,176 and 3,766,175; and (d) N-(phenylacetimidoyl)aminoacetamido as U.S. Pat. No. 3,692,779; and (e) α-amino-α-(1,4-cyclohexadienyl)acetamido as in Belgium Pat. No. 776,222 (Farmdoc 38983T; U.K. Pat. No. 1,328,340).

Additional similar disclosures are found in U.S. Pat. No. 3,692,779 (Belgium Pat. No. 771,189; Farmdoc 12819T), Japan Pat. No. 72/05550 (Farmdoc 12921T), Japan Pat. No. 72/05551 (Farmdoc 12922T), U.S. Pat. No. 3,719,673 (Belgium 759,570; Farmdoc 39819S), Belgium 793,311 (Farmdoc 39702U) and Belgium Pat. No. 793,191 (Farmdoc 39684U).

Issued disclosures of 3-thiolated cephalosporins in which the 7-substituent is 7-mandelamido (7-α-hydroxyphenylacetamido) are found, for example, in U.S. Pat. No. 3,641,021, France Pat. No. 73.10112, U.S. Pat. No. 3,796,801, Great Britain Pat. No. 1,328,340 (Farmdoc 38983T), U.S. Pat. No. 3,701,775, Japan Pat. No. 4844293 (Farmdoc 55334U) and in Hoover et al., J. Med. Chem. 17(1), 34–41 (1974) and Wick et al., Antimicrobial Ag. Chemo., 1(3), 221–234 (1972).

U.S. Pat. No. 3,819,623 (and, for example, also U.K. Pat. No. 1,295,841 and West Germany Pat. No. 1,953,861) discloses specifically and with working details the preparation of 2-mercapto-1,3,4-thiadiazole-5-acetic acid and its conversion to 7-(1H-tetrazol-1-ylacetamido)-3-(5-carboxymethyl-1,3,4-thiadiazol-2-ylthiomethyl)-3-cephem-4-carboxylic acid which is also disclosed in West Germany Offenlegungsschrift 2,262,262.

SUMMARY OF THE INVENTION

The present invention provides compounds having the structure:

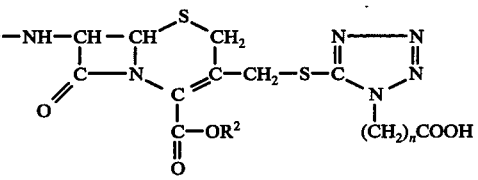

(often written herein as

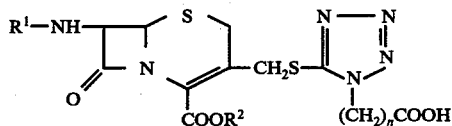

wherein n is one, two or three and $R^1$ is acyl or hydrogen and $R^2$ is hydrogen or the group having the formula

wherein, when W represents hydrogen, Z represents (lower)alkanoyl, benzoyl, naphthoyl, furoyl, thenoyl, nitrobenzoyl, methylbenzoyl, halobenzoyl, phenylbenzoyl, N-phthalimido, N-succinimido, N-saccharino, N-(lower)alkylcarbamoyl, (lower)alkoxy, (lower)-alkylthio, phenoxy, carbalkoxy, carbobenzoxy, carbamoyl, benzyloxy, chlorobenzyloxy, carbophenoxy, carbo-tert.-butoxy or (lower)alkylsulfonyl, and when W represents carbalkoxy, Z represents carbalkoxy and, when W represents phenyl, Z represents benzoyl or cyano or wherein W and Z taken together represent 2-oxocycloalkyl containing 4 to 8 carbon atoms inclusive. In the preferred embodiments of this invention $R^2$ is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl.

As set forth below in more detail the present invention also provides salts of these acids. The stereochemistry of the bicyclic nucleus is that found in Cephalosporin C.

Acyl (R¹) comprises the groups having the structures:

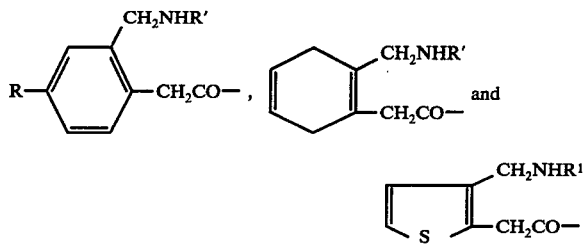

wherein R is hydrogen, hydroxy or methoxy and R' is hydrogen or methyl.

A preferred embodiment of the present invention consists of the compounds of Formula I wherein R¹ has the structure

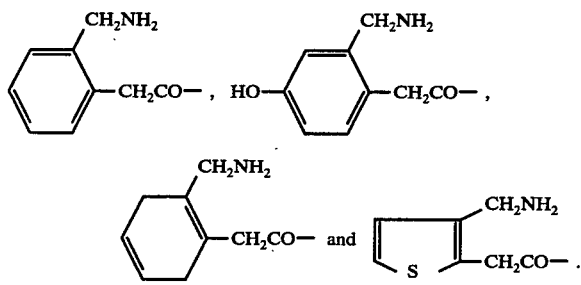

Another preferred embodiment of the present invention consists of the compounds of Formula I wherein R¹ has the structure

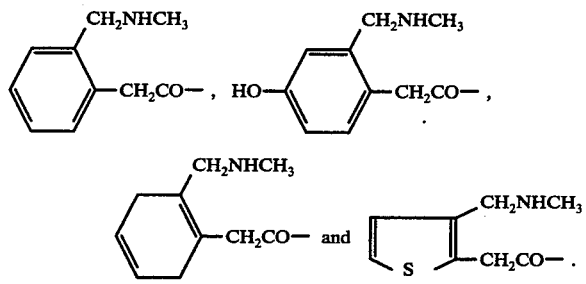

The present invention also provides the process for the production of the antibacterial agents having the structure

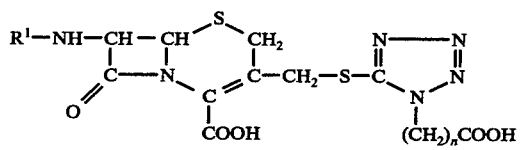

wherein R¹ is acyl as defined above and n is one, two or three which comprises reacting a compound of the formula

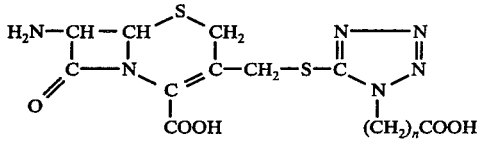

wherein n is one, two or three or a salt or easily hydrolyzed ester or Schiff base as with benzaldehyde or salicylaldehyde thereof (including, but not limited to, those of U.S. Pat. No. 3,284,451 and U.K. Pat. No. 1,229,453 and any of the silyl esters described in U.S. Pat. No. 3,249,622 for use with 7-aminopenicillanic acid and used in Great Britain Pat. No. 1,073,530 and particularly the pivaloyloxymethyl, acetoxymethyl, methoxymethyl, acetonyl, phenacyl, p-nitrobenzyl, β,β,β-trichloroethyl, 3-phthalidyl and 5-indanyl esters) thereof with an organic monocarboxylic acid chloride or a functional equivalent thereof as an acylating agent.

Such functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. In addition, an acid azide or an active ester or thioester (e.g. with p-nitrophenyl, 2,4-dinitrophenol, thiophenol, thioacetic acid) may be used or the free acid itself may be coupled with compound II after first reacting said free acid with N,N'-dimethylchloroformiminium chloride [cf. Great Britain 1,008,170 and Novak and Weichet, Experientia XXI, 6, 360 (1965)] or by the use of enzymes or of an N,N'-carbonyldiimidazole or an N,N'-carbonylditriazole [cf. South African patent specification 63/2684] or a carbodiimide reagent [especially N,N'-dicyclohexylcarbodiimide. N,N'-diisopropylcarbodiimide or N-cyclohexyl-N'-(2-morpholinoethyl)carbodiimide; cf. Sheehan and Hess, J. Amer. Chem. Soc., 77, 1967 (1955)], or of alkylylamine reagent [cf. R. Buijle and H. G. Viehe, Angew, Chem. International Edition 3, 582, (1964)] or of an isoxasolium salt reagent [cf. R. B. Woodward, R. A. Olofson and H. Mayer, J. Amer. Chem. Soc., 83, 1010 (1961)], or of a ketenimine reagent [cf. C. L. Stevens and M. F. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield dimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various microorganisms, e.g. those described by T. Takahashi et al., J. Amer. Chem. Soc., 94(11), 4035–4037 (1972) and by T. Nara et al., J. Antibiotics (Japan) 24(5), 321–323 (1971) and in U.S. Pat. No. 3,682,777.

For the coupling of the organic carboxylic acid as described above with compound II (or a salt or preferably an easily hydrolyzed ester of Schiff base, as with benzaldehyde, thereof) it is also convenient and efficient to utilize as the coupling agent phosphonitrilic chloride trimer (J. Org. Chem., 33(7), 2979–81, 1968) or N-ethoxy-1,2-dihydroquinoline (EEDQ) as described in J. Amer. Chem. Soc., 90, 823–824 and 1652–1653 (1968) and U.S. Pat. No. 3,455,929. The reaction is preferably carried out at 30°–35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a 7-acylaminocephalosporanic acid (prepared by substituting 7-amino-cephalosporanic acid for the 3-thiolated-7-amino-cephalosporanic acids in the acylation procedures described herein and elsewhere reported) with a thiol $HSR^3$ having the formula

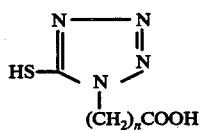

wherein $n$ is one, two or three and then removing the protecting group if any is present, as on the aminomethyl or methylaminomethyl group or on the carboxyl group or both. The displacement of such a 3-acetoxy group with such a thiol may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. As noted above, the preparation of many other 7-acylamidocephalosporanic acids is described in the patent and scientific literature, e.g. in U.S. Class 260-243C.

When the organic carboxylic acid contains a functional group such as amino or methylamino it is often desirable to first block (or protect) said group, then carry out the coupling reaction and finally subject the resulting compound to chemical removal of the protecting group, that is, subjecting the resulting compound to elimination reaction of the protecting group.

The salts of the compounds of this invention include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)-alkylpiperidine, e.g. N-ethylpiperidine, and other amines which have been used to form salts with benzylpenicillin;

Also included in this invention are the compounds (used as either intermediates or metabolic precursors) in which the amino group is "blocked" by substituents such as 2-iodoethoxycarbonyl (U.K. Pat. No. 1,349,673), t-butoxycarbonyl, carbobenzyloxy, formyl, o-nitrophenylsulfenyl, $\beta,\beta,\beta$-trichloroethoxycarbonyl, 4-oxo-2-pentenyl-2, 1-carbomethoxy-1-propenyl-2- and the like. Particularly included in such blocking groups are the ketones (especially acetone) and aldehydes (especially formaldehyde and acetaldehyde) disclosed, for example, in U.S. Pat. Nos. 3,198,804 and 3,347,851 and the $\beta$-ketoesters and $\beta$-diketones disclosed, for example, in U.S. Pat. No. 3,325,479 and the $\beta$-ketoamides disclosed in Japan Pat. No. 71/24714 (Farmdoc 47,321S).

The preferred esters of the cephalosporins of the present invention are the pivaloyloxymethyl, acetoxymethyl, methoxymethyl, acetonyl and phenacyl esters. All are useful intermediates in the production of the cephalosporin having a free carboxyl group.

As indicated above, these five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767–773 (1971). In another good method the triethylamine salt of 7-aminocephalosporanic acid is reacted directly with the active halogen compound, as in United Kingdom Pat. No. 1,229,453.

These esters of 7-aminocephalosporanic acid are then reacted with the nucleophile $HSR^3$ in the same manner as is illustrated herein for 7-aminocephalosporanic acid itself. The 3-thiolated ester of 7-aminocephalosporanic acid is then coupled with the organic carboxylic acid R'—OH as before. Before or after removal of any blocking group, e.g. on an amino group in the 7-sidechain, the ester of the cephalosporin so obtained is, if not used per se, converted to its free acid, including its zwitterion (and, if desired, any salt) by removal of the esterifying group, as by aqueous or enzymatic hydrolysis (as with human or animal serum) or acidic or alkaline hydrolysis or by treatment with sodium triophenoxide as taught in U.S. Pat. No. 3,284,451 and, in the penicillin series, by Sheehan et al., J. Org. Chem. 29(7), 2006–2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

In the treatment of bacterial infections in man, the compounds of this invention are administered parenterally in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excepients. The dosage units are in the form of liquid preparations such as solutions or suspensions.

STARTING MATERIALS

1-Carboxymethyl-5-mercaptotetrazole

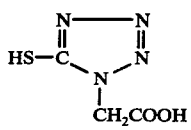

(a) Recrystallization of 1-methyl-5-mercaptotetrazole

Procedure:

1. One hundred and ten grams of 1-methyl-5-mercaptotetrazole is slurried in 350 ml. of boiling chloroform. A near solution is obtained.

2. The hot solution (50°-60°) is rapidly filtered by vacuum through a heated Buchner funnel (11 cm. SS No. 604 paper containing ¼ to ⅓ inch of packed filter aid ("Supercel"). The filter pad is washed with 50 ml. of 50°-60° C. chloroform which is added to the filtrate.

3. The filtrate is cooled to approximately 0°-6° C. and kept at 0°-6° C. for 2 hours. The crystals which have formed are collected by filtration at 0°-6° C. and washed with 60 ml. of 0°-6° C. chloroform which is added to the filtrate. The crystals (cut A) are air dried at 37°-45° C. for 18 hours.

4. The filtrate is concentrated on the rotary vacuum evaporator (60° C. bath) to approximately one-half volume. This slurry is cooled to 0°-6° C. and kept at 0°-6° C. for 2 hours. The crystals are collected by filtration at 0°-6° C., washed with 40 ml. of 0°-6° C. chloroform which is added to the filtrate. The crystals (cut B) are air dried at 37°-45° C. for 18 hours. Crystal cuts A and B are composited to give an approximate 65% weight yield.

The filtrate of cut B, Step 4 may be reworked twice as described in Step 4 to obtain an additional 15% recovery.

(b) Preparation of the Di-sodium Salt of 1-carboxymethyl-5-mercaptotetrazole

Procedure

1. Five hundred ml. of substantally dry and pure tetrahydrofuran in a 2-liter 3 neck flask with stirrer is cooled in a salt-acetone-ice bath to approximately −10° C. Dry nitrogen gas is blown on the liquid surface.

2. Five hundred ml. of 15.06% (1.6 N) butyl lithium in hexane (Foote Mineral Co.) is added over a ten minute period under dry nitrogen and stirring to the tetrahydrofuran. The near solution is cooled to −5° to −10° C.

3. Forty six and four tenths gram (46.4 g.) of 1-methyl-5-mercaptotetrazole (recrystallized as above) is dissolved in 200 ml. of substantially pure and dry tetrahydrofuran. The solution is filtered if cloudy and then cooled to 5° to 10° C.

4. The cooled solution of step 3 is added over 10 minutes with stirring and under dry nitrogen to the butyl lithium solution. The temperature should be maintained at −5° C. to +10° C. maximum. Precipitates may form.

5. The mixture is stirred under dry nitrogen and 0° C. to +10° C. for one half hour.

6. Anhydrous carbon dioxide gas is bubbled through at a rapid rate and with rapid stirring for 15-30 minutes at approximately ambient temperature (0° to 10° C.) to no higher than +20° C.

7. The white precipitate which forms is suitably collected by filtration in an area of low humidity. The precipitate is washed with about 75 ml. of tetrahydrofuran.

8. The precipitate is dissolved in 250 ml. of water (pH 8.5-9.5). A second layer of tetrahydrofuran may be present. This may be removed in the vacuum rotary evaporator (50° C. bath).

9. The aqueous solution is adjusted to pH 1.6-2.0 with concentrated hydrochloric acid.

10. The acid aqueous solution is extracted twice with 250 ml. portions of ethyl acetate. Each 250 ml. ethyl acetate extract is back extracted with 100 ml. portions of water. The water extracts are discarded. The ethyl acetate extracts (free of any water layer) are filtered and composited.

11. The combined ethyl acetate extracts are concentrated to dryness on the vacuum rotary evaporator (60° C. bath).

12. The crystals in the flask are boiled with 300 ml. of chloroform for about 2 minutes. The hot slurry (50°-60° C.) is vacuum filtered through a heated Buchner funnel (11 cm-SS-604 paper). The crystals are washed with about 75 ml. of 50° C. chloroform. The crystals are air dried at room temperature for about 3 hours and then made about 100-200 mesh.

13. The 100-200 mesh crystals are treated with boiling chloroform exactly as described in step 12 (the hot chloroform removes most of the unreacted 1-methyl-5-mercaptotetrazole). Yield: approximately 45 to 50 grams of crystalline 1-carboxymethyl-5-mercaptotetrazole. These crystals may contain 0.02 to 0.05 moles of 1-methyl-5-mercaptotetrazole.

14. The crystals of step 13 are slurried with 250 ml. of ethyl ether at room temperature for 3-5 minutes. The mixture is filtered. The insolubles (0.5-5%) may be a contaminating symmetrical mercaptotetrazole ketone of the following tentative structure:

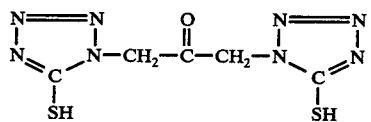

CAUTION: This compound EXPLODES at approximately 205°-210° C.

15. The ether filtrate of step 14 is evaporated to dryness on the vacuum rotary evaporator (50° C. bath). Approximately 42 to 48 grams of crystalline 1-carboxymethyl-5-mercaptotetrazole containing approximately 0.01-0.05 mole of 1-methyl-5-mercaptotetrazole is recovered.

16. The crystals are dissolved in 420 ml. of absolute ethanol (approximately 100 mg./ml.). The solution is warmed to 50°-60° C.

17. To the hot solution of step 16, 310 ml. of a 41% sodium 2-ethylhexanoate (SEH) solution in isopropanol is added with very rapid stirring over a 10 minute period. A crystalline precipitate forms. The mixture is slurried at 50°-60° C. for 20 minutes.

18. The mixture is filtered hot (50-60° C.) through a heated Buchner funnel (11 cm-SS-No. 604 paper). The crystals are washed with 75 ml. of 50° C. ethanol.

19. The ethanol damp crystals of step 18 are slurried in 200-300 ml. of ethanol. The slurry is passed through a 200 mesh screen. The slurry is heated to 50°-60° C. for 5 minutes with rapid stirring (unreacted mono-sodium 1-methyl-5-mercaptotetrazole is very soluble in hot ethanol).

20. The crystals are collected at 50°-60° C. on a 11 cm-SS No. 604 paper in a heated Buchner funnel. The crystals are washed with 75-100 ml. of ethanol and vacuum dried at 50°-60° C. for 24-48 hours. Yield: 40-48 grams of di-sodium 1-carboxymethyl-5-mercaptotetrazole (free of 1-methyl-5-mercaptotetrazole as observed by NMR).

7-Amino-3-(1-carboxymethyltetrazol-5-yl-thiomethyl)-3-cephem-4-carboxylic acid.

9. Air dry the solid to constant weight. (A typical run produced 14.5 grams of product.) This product may vary in color from yellow to dark brown.

10. Pass the product through a 200 mesh stainless steel screen.

11. Suspend 10 grams of the 200 mesh powder in 200 ml. of n-propanol with rapid stirring.

12. Add 2.0 ml. of concentrated hydrochloric acid and stir vigorously for 0.5 hour at room temperature.

13. Filter the slurry. Wash the brown solids with 20 ml. of n-propanol and add the wash to the filtrate (save the filter cake for possible recovery of additional product).

14. Add 1.5 grams of charcoal ("Darco G-60") to the n-propanol filtrate of step 13. Slurry for 0.5 hour. Remove the carbon by filtration. Wash the carbon with 20 ml. of n-propanol and add the wash to the filtrate.

15. With rapid stirring, add triethylamine to the n-propanol filtrate to an apparent pH of 3.0. Crystals form. Slurry for 10 minutes.

16. Collect the white crystals by filtration and wash with 30 ml. of n-propanol, 50 ml. of methanol, and vac-

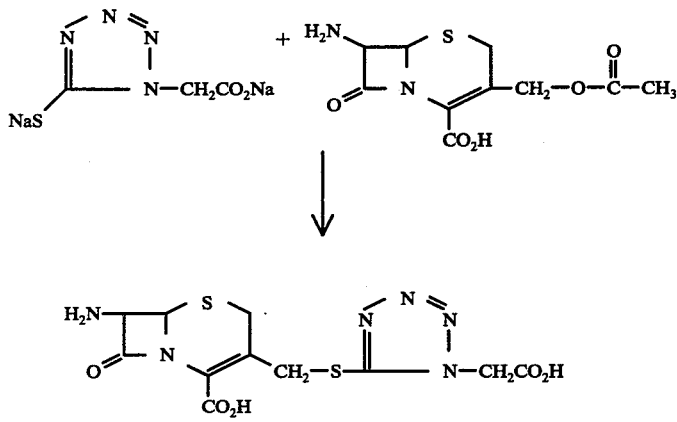

1. Into a 3 necked flask set up with an agitator, a temperature regulator, thermometer and a nitrogen inlet tube, place 18 grams (0.066 mole) of 7-aminocephalosporanic acid, (which has preferably been recrystallized by the toluenesulfonic acid procedure) and 300 ml. of 0.1 M pH 6.4 phosphate buffer (20.7 grams of sodium phosphate, monobasic 0.1H$_2$O + 8.5 grams of sodium phosphate, dibasic, anhydrous, q.s. to 2 liters).

2. With agitation of the mixture described in step 1, add 1.5 grams of sodium bisulfite and 16 grams (0.078 moles) of 1-carboxymethyl-5-mercaptotetrazole disodium.

3. With agitation continuing, bubble nitrogen through the mixture for 10 minutes.

4. Maintaining agitation and nitrogen inflow, heat the slurry over a 20 minute period to 56° C. During this time interval, 6.5 grams of sodium bicarbonate is added in small increments.

5. With continued agitation and nitrogen inflow, maintain the temperature of the solution at 56° C. for 4 hours. The pH should remain at between 6.2 – 6.6.

6. Cool the reaction mixture in an ice bath to 5° C.

7. Add 50 ml. of a 1:1 phosphoric acid/water solution to the mixture or concentrated HCl to a pH of 2.0 – 3.0.

8. Collect the product by filtration. Wash the filter cake with 20 ml. of cold water followed by 200 ml. of cold methanol.

uum dry at 40° C. for 24 hours. Yield: 4 to 8 grams of 7-amino-3-(1-carboxymethyltetrazol-5-ylthiomethyl)-3-cephem-4-carboxylic acid.

17. An alternate procedure for the purification of 7-amino-3-(1-carboxylmethyltetrazol-5-ylthiomethyl)-3-cephem-4-carboxylic acid follows:

(a) Slurry 10 grams of the 200 mesh product (from step 10) in 75 ml. of 1 N hydrochloric acid for 10–15 minutes at room temperature. Filter to remove dark brown solids.

(b) Add 2.5 grams of charcoal ("Darco G-60") and slurry for 0.5 hour.

(c) Remove the carbon by filtration. Wash the carbon with 15 ml. of water and add the wash to the filtrate.

(d) With rapid stirring, add concentrated ammonium hydroxide to the filtrate to pH 2.5-3.0. Crystals form.

(e) Slurry the crystal mass for 25 minutes. Remove the crystals by filtration. Wash the crystals with 30 ml. of water, 50 ml. of methanol, and vacuum dry at room temperature. Yield: 4-7 grams of near white crystals.

The other reagents used to prepare the compounds of the present invention are synthesized either as described in the art (e.g. as in the patents and publications noted above) or by strictly analogous procedures. For convenience and purposes of illustration, however, there are given below some specific examples of such syntheses, e.g. to prepare carboxylic acids containing a free amino group which is "blocked" with tert.-butoxycarbonyl.

2-(tert.-Butoxycarbonylaminomethyl)-1,4-cyclohexadienylacetic acid

A solution of 16.5 g. (0.1 mole) of o-amino-methylphenylacetic acid in 1.5 l of liquid ammonia (which had been treated with 50 mg. of Li to remove a trace of moisture) was slowly diluted with 500 ml. of dry t-BuOH. To the solution was added in small portions 3.4 g. (0.5 atom) of Li over a period of 4 hours and the mixture was stirred for 16 hours at room temperature removing the liquid ammonia in a hood and finally evaporated to dryness below 40° C. The residue was dissolved in 500 ml. of water and the solution was chromatographed on a column of IR-120 (H+, 700 ml.) resin and eluted with 1% NH$_4$OH solution. Ninhydrin positive fractions of the eluate were combined and evaporated to dryness. The residue was washed with four 50 ml. portions of hot acetone and recrystallized from 500 ml. of ethanol-water (1:1) to give 11.2 g. (67%) of colorless needles, o-(2-aminomethyl-1,4-cyclohexadienyl)acetic acid. M.p. 183° C.

IR $\gamma_{max}^{nuj}$ 1630, 1520, 1380, 1356 cm$^{-1}$. NMR: $\delta^{D_2O}$ + $K_2CO_3$ 2.72 (4H, s, H$_2$C<=), 3.01 (2H, s, CH$_2$CO), 3.20 (2H, s, CH$_2$—N), 5.78 (2H, s, $^H$>C=).

Anal. Calcd. for C$_9$H$_{13}$NO$_2$: C, 64.65; H, 7.84; N, 8.38. Found: C, 64.77; H, 8.06; N, 8.44.

Improved Procedure for the Preparation of o-(2-aminomethyl-1,4-cyclohexadienyl)-acetic acid

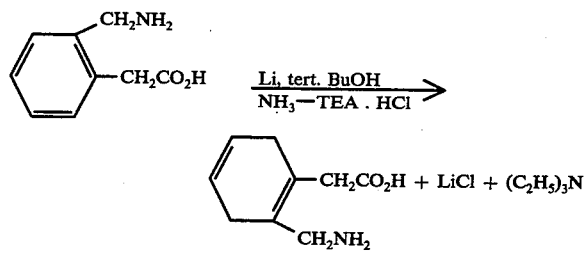

The procedure used by Welch, Dolfini and Giarrusso in U.S. Pat. No. 3,720,665 (Example 1) to make D-2-amino-2-(1,4-cyclohexadienyl)acetic acid was adapted. A solution of 830 ml. of distilled liquid ammonia was dried with 40 mg. of lithium under an argon atmosphere. To this stirred solution was added 11.0 g. (0.07 mole) of 2-aminomethylphenylacetic acid and 340 ml. of tert. butyl alcohol. A total of 1.6 g. (0.225 mole) of lithium was added to the vigorously stirred solution over a period of 2 hours. The grey mixture was then treated with 35 g. (0.215 mole) of triethylamine (TEA) hydrochloride and stirred overnight at room temperature for 18 hours. The tert. butyl alcohol was removed at 40° (15 mm.) to yield a white residue which was dried in vacuo over P$_2$O$_5$ overnight. The solid was dissolved in 30 ml. of 1:1 methanol-water and added with stirring to 3.5 l. of 1:1 chloroform-acetone at 5°. The mixture was stirred for 20 min. and the amino acid, α-(2-aminomethyl-1,4-cyclohexadienyl)acetic acid, was collected and dried for 16 hours in vacuo over P$_2$O$_5$ to yield 6.3 g. (58%) of white crystals, m.p. 190° decomp. The IR and NMR spectra were consistent for the structure.

A solution of 19.31 g. (0.135 m) of tert.-butoxycarbonylazide in 152 ml. of tetrahydrofuran (THF) was added to a stirred solution of 14.89 g. (0.09 m) of 2-aminomethyl-1,4-cyclohexadienylacetic acid and 7.20 g. (0.18 m) of sodium hydroxide in 281 ml. of water. The solution was stirred for 18 hr. at 25° and then filtered thru diatomaceous earth (Super-cel). The THF was removed at 40° (15 mm) and the residual solution was washed with ether (2 × 175 ml.) and acidified with 6 N hydrochloric acid (HCl). The mixture was stirred in an ice-bath and the precipitate was collected and dried for 18 hr. in vacuo over P$_2$O$_5$ at 25° to yield 17.3 g. (72.6%) of 2-(tert.-butoxycarbonylaminomethyl)-1,4-cyclohexadienylacetic acid as a white powder. The IR and NMR spectra were consistant for the structure.

PREPARATION OF 1-CARBOXYETHYLTETRAZOL-5-THIOL

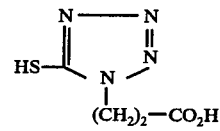

(A) 2-Carboethoxyethylisocyanate

β-alanine ethyl ester hydrochloride (93.6 g.), triethylamine (123.5 g.) and methylene chloride (400 ml.) were mixed together and cooled to −10° C. Carbon disulfide (46.5 g.) dissolved in 150 ml. of chloroform was added to the above solution during a two-hour period while keeping the temperature at about −10° C. After the addition was complete, the temperature was allowed to warm to 10° C. for about 10 minutes. The solution was again cooled to −10° C. and 66.3 g. of ethyl chloroformate in 60 ml. of chloroform was added dropwise over a 40-minute period with stirring. The temperature was allowed to rise to room temperature for 30 minutes and again cooled to 0° C.; an additional 61.6 g. of triethylamine was added at 0° C. and then the solution was stirred at room temperature for 3 hours.

The mixture was treated with water and the organic phase collected, washed with 2 × 250 ml. of 2N HCl, then 2 × 250 ml. of NaHCO$_3$, then 2 × 250 ml. of water. The organic phase was dried over Na$_2$SO$_4$ and the solvent removed in vacuo to produce 93.7 g. of an oil found to be the desired product. The IR and NMR spectra were consistent with the structure.

(B) 1-Carboxyethyltetrazol-5-thiol

Sodium azide (29.7 g.) was dissolved in 400 ml. of water and heated to 60° C. in a nitrogen atmosphere. 2-Carboethoxyethylisocyanate (46.9 g.) dissolved in 50 ml. of Skellysolve B (essentially n-hexane) was added to the heated sodium azide solution. The solution was stirred for about 150 minutes at about 70°-72° C., then cooled to 30° C. in an ice bath. Fifty percent sodium hydroxide solution was added until the pH was 12. The mixture was heated for 40 minutes at 70° C. and cooled to 15° C. in an ice bath. The pH was adjusted to 2 using concentrated HCl and then extracted with ethyl acetate (4 × 150 ml.). The ethyl acetate extracts were washed with water, then dried over sodium sulfate. The solvent was evaporated in vacuo and the product was collected as crystals from methylene chloride to yield 19.5 g. of title product.

PREPARATION OF 1-CARBOXYALKYLTETRAZOL-5-THIOL

Substitution in the procedure for the preparation of 1-carboxyethyltetrazol-5-thiol for the β-alanine ethyl ester used therein of an equimolar quantity of an appropriately substituted amino acid ester of 4 to 10 carbon atoms produces the corresponding 1-carboxy($C_1$-$C_9$ alkyl)tetrazol-5-thiol; e.g., 1-carboxypropyltetrazol-5-thiol,
1-carboxybutyltetrazol-5-thiol,
1-carboxypentyltetrazol-5-thiol,
1-carboxyhexyltetrazol-5-thiol,
1-carboxyheptyltetrazol-5-thiol,
1-carboxyoctyltetrazol-5-thiol, and
1-carboxynonyltetrazol-5-thiol.

PREPARATION OF 3-AMINOMETHYL-2-THIOPHENE ACETIC ACID

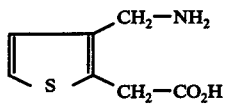

(A) Thiophene-3-carboxaldehyde Dimethyl Acetal (2a)

A mixture of thiophene-3-carboxaldehyde[1] (322 g., 1.9 moles), trimethoxymethane (636 g., 6 moles) and IR-120 resin ($H^+$, 6 g.) in methanol (200 ml.) was refluxed over a period of 4 hours. The resin was removed and the filtrate was evaporated under reduced pressure to give a colorless oil which was distilled under reduced pressure. Yield 423 g. (94%), b.p. 90°–95° C. 13 mmHg.
[1] S. gronowitz, Arkev. kemi., 8, 411 (1955).

ir: $\eta_{max}^{liq}$ 3150, 1045, 1025 $cm^{-1}$ nmr: $\delta_{ppm}^{neat}$ 3.21 (6H, s, $OCH_3$), 5.43 (1H, s,

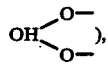

7.0–7.4 (3H, m, thiophene-H)

(B) 2-Formylthiophene-3-carboxaldehyde Dimethylacetal (3a)

To a stirred solution of 2a (423 g., 2.68 moles) in anhydrous ether (1 L) was added dropwise in 1 hour a freshly prepared solution of n-butyllithium (27 moles) in ether keeping a gentle reflux under dry $N_2$. Reflux being continued for 0.5 hour, a solution of DMF (dimethylformamide) (432.5., 6 moles) in anhydrous ether (0.8 L) was added dropwise to the mixture over a period of 0.75 hour with vigorous stirring. After the complete addition the mixture was stirred overnight, poured onto crushed ice (1 Kg.) with stirring and allowed to rise to room temperature. The organic layer was separated and the water layer was saturated with NaCl and extracted thoroughly with ether (2 × 200 ml.). The ether extracts were combined, dried over $MgSO_4$ and concentrated. The residue was distilled under reduced pressure and the pale yellow oil was collected at 100°–125° C., 0.7 mmHg. Yield, 277 g. (56%).

ir: $\eta_{max}^{liq}$ 3110, 1660, 1100 $cm^{-1}$. nmr: $\delta_{ppm}^{neat}$ 3.40 (6H, s, $OCH_3$), 5.86 (1H, s,

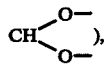

7.27 (1H, d, J=6Hz, thiophene-H3), 7.81 (1H, d—d, J=6Hz, thiophene-Hz), 10.34 (1H, d, J=1, 5Hz, —CHO).

(C) 1-Methylsulfinyl-1-methylthio-2-(3-carboxaldehyde Ethylene (4b)

Preparation of 4b was carried out according to the procedure similar to that reported by K. Ogura et al.[4]. Triton B (40% in methanol, 2 ml. in THF (tetrahydrofuran) (5 ml.) was added to a solution of methyl methylthiomethyl sulfoxide[2] (2.5 g., 20 m. moles) and 2-formyl-3-thiophenecarboxaldehyde ethylene acetal[3] (3b). The mixture was refluxed for about one hour and concentrated under reduced pressure. The residue was dissolved in benzene (150 ml.) and extracted with water (3 × 20 ml.). The organic layer was dried over $MgSO_4$ and evaporated to dryness under reduced pressure.
[2] K. Ogura, et al., Bull. Chem. Soc. (Japan), 45, 2203 (1972)
[3] D. W. McDowell et al., J. Org. Chem. 31, 3592 (1966)
[3] K. Ogura, et al., Tetrahedron Letters, 1383 (1972).

The residue was dissolved in benzene (150 ml) and extracted with water (3 × 20 ml). The organic layer was dried over $MgSO_4$ and evaporated to dryness under reduced pressure. The residue was column-chromatographed on silica gel (80 g) eluting with benzene (500 ml) and chloroform (100 ml) successively. From the chloroform eluate 4.9 g (85%) of the product 4b was isolated as a pale yellow oil.

ir: $\eta_{max}^{liq}$ 3110, 1600 $cm^{-1}$. nmr: $\delta_{ppm}^{CDCl_3}$ 2.42 (3H, x, S-$CH_3$), 2.78 (3H, s, SO—$CH_3$), 4.15 (4H, m, $CH_2CH_2$—), 6.12 (1H, s,

7.34 (1H, d, J=4.5Hz, thiophene-Hβ), 7.40 (1H, d, J=4.5Hz, thiophene-Hα), 8.28 (1H, s, —CH=).

The semicarbazone of 4 was prepared by a usual manner and crystallized from ethanol-DMF. M.p. 212°–213° C.

Anal. Calcd. for $C_{10}H_{13}N_3O_2S_2$: C, 39.58; H, 4.32; N, 13.85; S, 31.70. Found: C, 39.46; H, 4.24; N, 14.05; S, 31.63.

(D) 1-Methylsulfinyl-1-methylthio-2-(3-carboxaldehyde dimethylacetal-2-thienyl)ethylene (4a).

The compound 4a was prepared by the procedure similar to that for 4b. Triton B (40% in methanol, 50 ml) was added to a solution of methyl methylthio-methylsulfoxide (72 g., 0.58 mole) and 3a (108 g, 0.58 mole) in THF (300 ml) and the mixture was refluxed for 4 hours. Separation by column chromatography with silica gel (400 g) eluting with chloroform (5 L) gave 130.5 g (78%) of 4a as a pale yellow oil.

ir: $\eta_{max}^{liq}$ 3100, 1580, 1100, $1050^{-1}$. nmr: $\delta_{ppm}^{CCl_4}$ 2.42 (3H, s, S—$CH_3$), 2.70 (3H, s, SO—$CH_3$), 3.34 (6H, s, $OCH_3$), 5.56 (1H, s, $CH_O^O$), 7.20 (1H, d, J=6Hz, thiophene-Hβ), 7.40 (1H, d, J=6Hz, thiophene-Hα), 8.12 (1H, s, —CH=).

(E) Ethyl 3-formyl-2-thienylacetate[4] (5)

Dry hydrogen chloride (33 g) was absorbed in anhydrous ethanol (500 ml). To this solution 4a (130 g, 0.45 mole) was added and the mixture heated under reflux for 5 mins. The reaction mixture was diluted with water and evaporated under reduced pressure. The residue was extracted with benzene (2 × 100 ml) and the benzene extracts were combined, washed with water (50 ml), dried over $MgSO_4$ and evaporated to dryness. The oily residue was column-chromotographed on silica gel (400 g) eluting with chloroform (5 L). Fractions containing the desired product were combined and concentrated. The residual oil (60 g) was distilled under reduced pressure to afford 23 g (23%) of 5, boiling at 120°-126° C/1 mmHg.

ir: $\eta_{max}^{liq}$ 3110, 1730, 1670 cm$^{-1}$. nmr: $\delta_{ppm}^{CDCl_3}$ 1.30 (3H, t, J=6Hz, —CH$_2$CH$_3$), 4.25 (2H, q, J=6Hz, —CH$_2$CH$_3$), 4.26 (2H, s, —CH$_2$CO), 7.25 (1H, d, J=5Hz, thiophene-H$\beta$), 7.48 (1H, d, J=5Hz, thiophene-H$\alpha$), 10.15 (1H, s, CHO).

The analytical sample of 5 was submitted as the 2,4-dinitrophenylhydrazone which was crystallized from chloroform. M.p. 178°-179° C.

ir: $\eta_{max}^{nujol}$ 1720, 1610, 1570 cm$^{-1}$.

Anal. Calcd. for C$_{15}$H$_{14}$N$_4$O$_6$S: C, 47.62; H, 3.73; N, 14.81; S, 8.47; Found: C, 47.33; H, 3.47; N, 14.77; S, 8.68.

According to the similar procedure 2.2 g (7.6 m moles) of the ethylene acetal 4b was treated with 1.1 g of dry hydrogen chloride in 800 ml of anhydrous ethanol to afford 5 which was purified by column chromatography on silica gel (30 g). Elution with chloroform gave 663 mg (44%) of 5 as a pale yellow oil.

(F) Ethyl 3-formyl-2-thienylacetate oxime (6)

Sodium carbonate (1.7 g, 16 m mole) was added to a solution of the aldehyde 5, (3.14 g, 16 m mole) and hydroxylamine hydrochloride (2.2 g, 32 m mole) in 50% aq. ethanol (40 ml) at 5° C with stirring. The reaction mixture was warmed up to room temperature. After 2.5 hrs., the reaction mixture was concentrated under reduced pressure. The residue was extracted with benzene (3 × 50 ml). The benzene extracts were washed with water (10 ml), dried over MgSO$_4$, and evaporated under reduced pressure. Separation by column chromatography on silica gel (60 g) gave 2.7 g (80%) of colorless oil 6.

ir: $\eta_{max}^{liq}$ 3400, 1730, 1620 cm$^{-1}$. nmr: $\delta_{ppm}^{Aceton-d_6}$ 1.23 (3H, t, J=7.5Hz, —CH$_2$CH$_3$), 4.01 (2H, s, —CH$_2$CO), 4.14 (2H, q, J=7.5Hz, —CH$_2$CH$_3$), 7.31 (2H, s, thiophene-H), 8.26 (1H, s, —CH═N), 10.15 (1H, s, NOH, disappeared by addition of D$_2$O).

(G) The δ-lactam of 3-aminomethyl-2-thienylacetic acid (7)

Method A: Catalytic reduction

A mixture of the oxime 6 (2.65 g, 12.4 m moles), 10% palladium on charcoal, dry hydrogen chloride (1.4 g, 37.2 m moles) in anhydrous ethanol (68 ml) was hydrogenated overnight under atmospheric pressure at room temperature. The catalyst was exchanged twice and the reaction was carried out over a period of 3 days. The catalyst was removed and the filtrate was concentrated under reduced pressure. To the residue was added water (10 ml) and the mixture washed with ethyl acetate (2 × 10 ml). The aqueous layer was adjusted to pH 9 with sodium carbonate, saturated with sodium chloride, and extracted with ethyl acetate (3 × 20 ml). The ethyl acetate extracts were dried over MgSO$_4$, treated with charcoal, and evaporated under reduced pressure. Recrystallization from ethyl acetate gave 417 mg (22%) of colorless needles 7 melting at 194°-195° C.

ir: $\eta_{max}^{KBr}$ 3200, 1650, 1480 cm$^{-1}$. nmr: $\delta_{ppm}^{DMSO-d_6}$ 6 3.53 (2H, t, J=3Hz, —CH$_2$CO—), 4.36 (2H, d-t, J=3, 1.5Hz, changed to a triplet by addition of D$_2$O, J=3Hz, CH$_2$N), 6.95 (1H, d, J=4.5Hz, thiophene-H$\beta$), 7.45 (1H, d, J=4.5Hz, thiophene-H$\alpha$), 8.0 (1H, m, disappeared by addition of D$_2$O, NH).

Anal. Calcd. for C$_7$H$_7$NOS: C, 54.88; H, 4.61; N, 9.14; S, 20.93; Found: C, 55.04; H, 4.45; N, 9.13; S, 20.50.

Method B: Zn-dust reduction

To a solution of the oxime 6 (18.3 g, 86 m moles) in acetic acid (200 ml), zinc dust (17 g, 258 m moles) was added portionwise over a period of 1 hr. at 40°-50° C with vigorous stirring. The reaction mixture was stirred overnight at room temperature and heated at 60° C for 4 hours. The contents were filtered and the filtrate was concentrated under reduced pressure. To the residual oil was added water (100 ml) and the mixture washed with ether (2 × 50 ml). The aqueous solution was layered with ethyl acetate (100 ml) and adjusted to pH 10 with sodium carbonate. The precipitate was filtered off. The filtrate was extracted with ethyl acetate. The ethyl acetate extracts were washed with water (10 ml), dried over MgSO$_4$, and evaporated under reduced pressure. The residual solid was triturated with benzene. Crystallization from ethyl acetate gave 2.7 g (21%) of the lactam 7 which was identical to Method A in the IR and the NMR spectra.

(H) 3-Aminomethyl-2-thienylacetic acid (8)

A mixture of the lactam 7 (2.88 g, 18.8 m moles) and 6b hydrochloric acid (50 ml) was heated under reflux for 3 hrs. The reaction mixture was concentrated under reduced pressure. To the residue was added water (20 ml) and the mixture treated with charcoal and evaporated under reduced pressure. The trituration of the residue with THF gave the amino acid 8 hydrochloride (3.72 g, 95%; m.p. 171°-172° C; ir (KBr) cm$^{-1}$: 3450, 3000, 1700, 1200; nmr (D$_2$O)ppm: 4.80 (2H, s, —CH$_2$CO), 4.27 (2H, s, CH$_2$—N), 7.26 (1H, d, J=6Hz, thiophene-H$\beta$), 7.53 (1H, d, J=6Hz, thiophene-H$\alpha$). The hydrochloride (3.71 g, 17.9 m moles) was dissolved in water (10 ml) chromatographed on a column of IR-120 (H, 30 ml) and developed successively with water (100 ml) and 5N—NH$_4$OH (2L). The ammonia eluate was evaporated to dryness. The residue was crystallized from aqueous acetone to give 3.0 g (98%) of 8, m.p. 223°-225° C.

ir: $\eta_{max}^{HBr}$ 3000, 1620, 1520 cm$^{-1}$. nmr: $\delta^{D_2O-Na_2CO_3}$ 3.20 (sH, s, —CH$_2$OC), 4.13 (2H, s, CH$_2$N), 7.04 (1H, d, J=6Hz, thiophene-H$\beta$), 7.30 (1H, d, J-6Hz, thiophene-H$\alpha$).

Anal. Calcd. for C$_7$H$_9$NO$_2$S: C, 49.10; H, 5.30; N, 8.18; S, 18.73; Found: C, 48.53: h, 5.22; N, 7.98; S, 18.97.

(I) 3-t-Butoxycarbonylaminomethyl-2-thienylacetic acid (9)

A mixture of 3-aminomethyl-2-thienylacetic acid 8 (3.1 g, 18 m. moles) and triethylamine (8 g. 80 m moles) in 50% aqueous acetone (80 ml) was added dropwise t-butoxycarbonyl azide (5.7 g, 40 m moles) over a period of 20 mins. at 0° C with vigorous sitrring. The reaction mixture was stirred overnight at room temperature and concentrated under reduced pressure. The concentrate was washed with ether (2 × 20 ml), adjusted to pH 2 with conc. HCl and extracted with ethyl acetate (2 × 50 ml). The ethyl acetate extracts were washed with saturated aqueous sodium chloride, dried over MgSO$_4$, treated with charcoal and evaporated under reduced pressure. The residue was triturated with n-hexane and crystallized from n-hexane and benzene to give 4.5 g (92%) of colorless needles 9, melting at 62°-63° C.

ir: $\eta_{max}^{nujol}$ 3350, 1700 cm$^{-1}$. nmr: $\delta_{ppm}^{CDCl_3}$ 1.43 (9H, s, BOC—H), 3.27 (2H, s, CH$_2$CO), 4.16 (2H, d, J=6Hz, CH$_2$—N, a singlet when D$_2$O was added, 5.00 (1H, br, —NH—, disappeared by addition of D$_2$O), 6.30 (1H, broad s, —COOH, disappeared by addition of D$_2$O), 6.86 (1H, d, J=6Hz, thiophene-H$\beta$), 7.06 (1H, d, J=6Hz, thiophene-H$\alpha$).

Anal. Calcd. for C$_{12}$H$_{17}$NO$_4$S: C, 52.89; H, 6.29; N, 5.14; S, 11.77. Found: C, 53.30; H, 6.39; N, 5.13; S, 11.72.

(J) Alternate Synthesis of 1-Carboxymethyl-5-mercaptotetrazole

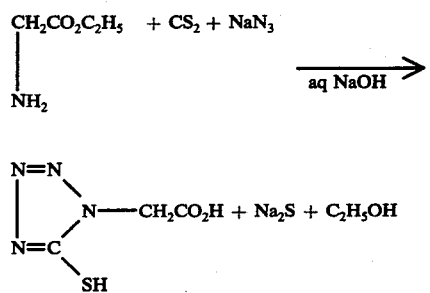

To a stirred mixture of 13.95 g (0.10 m) of glycine ethyl ester hydrochloride, 8.0 g. (0.20 m.) of sodium hydroxide and 8.37 g (0.11 m) of carbon disulfide was added a solution of 7.47 g (0.115 m) of sodium azide in 125 ml of water. The solution was heated at reflux for 6¼ hrs. and stored 16 hrs. at 25°. The dark brown mixture was filtered and the filtrate acidified to pH 1.5 with conc. hydrochloric acid. The solution was carbon treated and the yellow filtrate was extracted 4 × 100 ml with ethyl acetate. The ethyl acetate was washed with water, dried over magnesium sulfate and evaporated at 40° (15 mm) to an oil. The oil was triturated with methylene chloride and the product was collected. The sample was dried in vacuo over phosphorus pentoxide for 16 hrs. at 25°. The ir and nmr spectra were consistent for the structure.
Reference: German Patent 106645.

PREPARATION OF 5-MERCAPTOTETRAZOLE-1-ACETIC ACID FROM 2-CARBOETHOXYMETHYL ISOTHIOCYANATE

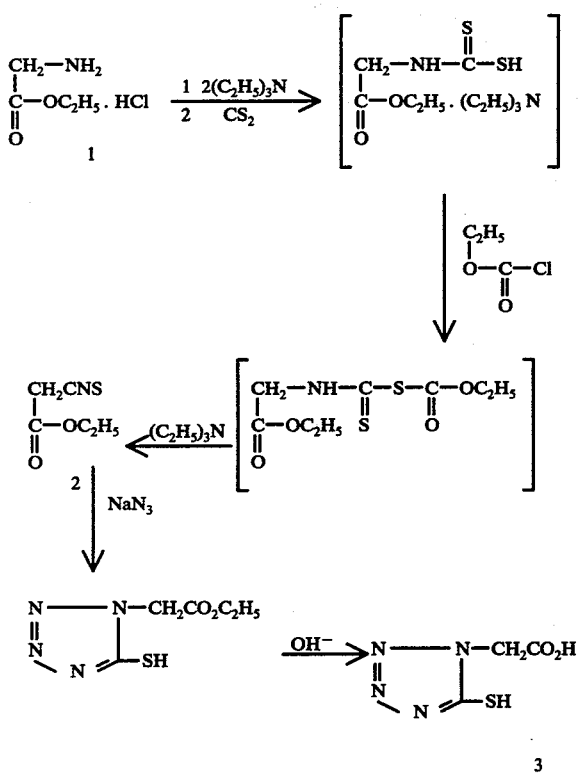

Carboethoxymethyl Isothiocyanate 2

Carbon disulfide (22.8 g., 0.3 mol.) in chloroform (40 ml.) was added over a period of one hour to a stirred suspension of glycine ethyl ester hydrochloride (41.7 g. 0.3 mol.) and triethylamine (60.7 g., 0.6 mol.) in methylene chloride (300 ml.) at −10° C. The reaction mixture was allowed to warm up to 10° C. and was stirred for 10 minutes at this temperature. The mixture was treated dropwise with ethyl chloroformate (32.6 g., 0.3 mol.) in chloroform (50 ml.) at 0°–5° C. over a period of 0.5 hour. The mixture was stirred for another 40 minutes at room temperature and triethylamine (30.4 g., 0.3 mol.) was added dropwise over a period of 15 minutes. The mixture was stirred for ¼ hour at 0° C. and an additional ½ hour at room temperature and finally stored over night at 25° C. The mixture was washed with water (250 ml.), 2N hydrochloric acid (2 × 300 ml.), 5% sodium bicarbonate solution (4 × 300 ml.) and dried over anhydrous sodium sulfate. The solvent was evaporated at 40° C. (15 mm.) to yield 38.1 g. of crude isothiocyanate. Upon storage overnight, a red dye was produced. This may be eliminated by distillation of the isothiocyanate.*

*The isothiocyanate may be distilled at 104°–106° C. (7 mm.) T. B. Johnson and A. G. Renfrew, JACS 47, 240–245 (1925)

5-Mercaptotetrazole-1-acetic acid 3

To a solution of sodium azide (4.9 g., 0.075 mol.) in water (100 ml.) heated to 60° C. under nitrogen, was added the isothiocyanate (7.3 g., 0.5 mol.) over a period of ¼ hour. The mixture was heated at 70°–75° C. for 2 hours, cooled to 5° C. and 50% sodium hydroxide was added to pH 12. The solution was heated to 75° C. for 1 hour, cooled to 5° C. and adjusted to pH 2 with concentrated hydrochloric acid and filtered through diatomaceous earth ("Supercel"). The solution was extracted with ethyl acetate (4 × 120 ml.), carbon treated and evaporated to an oil at 30° C. (15 mm.). The residue was slurried with chloroform to yield 1 g. of acid. The nmr and ir spectra were identical with authentic 5-mercaptotetrazole-1-acetic acid.

PREPARATION OF 2-N-METHYLAMINOMETHYL-4-METHOXY- (AND 4-HYDROXY-)PHENYLACETIC ACIDS

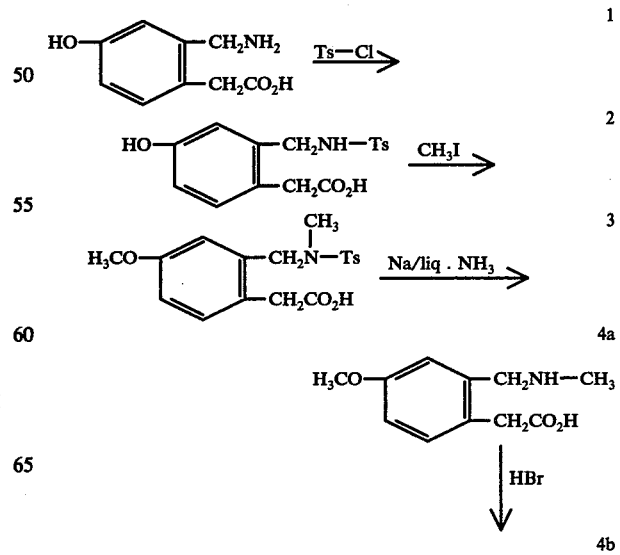

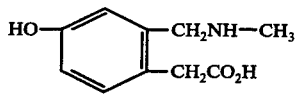

2-N-TOSYLAMINOMETHYL-4-HYDROXY-PHENYLACETIC ACID (2)

To a solution of 14.56 g. (0.08 mol.) of 2-aminomethyl-4-hydroxyphenylacetic acid (1) (U.S. 3,823,141) and 13 g. (0.32 mol.) of sodium hydroxide in 200 ml. of water was added dropwise with stirring at 65°–70° C. a solution of 18.5 g. (0.097 mol.) of p-toluenesulfonyl chloride in 50 ml. of dry ether and the mixture was kept at the same temperature for one hour. The mixture being cooled, the aqueous layer was separated, washed with ether (2 × 50 ml.), acidified with 6N HCl and extracted with 400 ml. of ethyl acetate. The extract was washed with water and a saturated aqueous NaCl solution, dried with $Na_2SO_4$ and treated with active carbon (1 g.). The filtrate was concentrated to dryness and the residue was crystallized from ethyl acetate to give 11.0 g. (40.5%) of 2 melting at 212°–215° C.

ir: $\eta_{max}^{KBr}$ 3240, 1700, 1380, 1330, 1150 cm$^{-1}$
uv: $\lambda_{max}^{1\%K_2CO_3}$ 230 nm ($\epsilon$: 7,750)
nmr: $\delta_{ppm}^{DMSO-d_6}$ 2.47 (3H, s, Ar-CH$_3$), 3.60 (2H, s, CH$_2$CO), 3.93 (2H, d, J=6.0 Hz, CH$_2$N), 6.6–8.2 (7H, m, phenyl-H).

2-(N-METHYL-N-TOSYLAMINO)METHYL-4-METHOXYPHENYLACETIC ACID (3)

A mixture of 11 g. (0.033 mol.) of 2, 10.3 ml. (0.17 mol.) of methyl iodide and 9.2 g. (0.24 mol.) of sodium hydroxide in 100 ml. of water was heated at 80°–90° C. for 45 minutes in a sealed tube with occasional shaking. The mixture was washed with ethyl acetate (30 ml.) and the water layer was acidified with 6N HCl and extracted with ethyl acetate (3 × 30 ml.). The combined extracts were washed with water (30 ml.) and a saturated aqueous NaCl solution (30 ml.) treated with active carbon (1 g.) and dried over $Na_2SO_4$. The filtrate was evaporated to dryness and the residue was crystallized from benzene to give 8 g. (66.5%) of the N,O-dimethyl derivative 3 melting at 146°–150° C.

ir: $\eta_{max}^{KBr}$ 1690, 1500, 1340, 1280, 1150 cm$^{-1}$.
uv: $\lambda_{max}^{EtOH}$ 229 nm ($\epsilon$: 20500), 278 nm ($\epsilon$: 2400).
nmr: $\delta_{ppm}^{DMSO-d_6}$ 2.52 (3H, s, N-CH$_3$), 2.47 (3H, s, Ar-CH$_3$), 3.67 (2H, s, CH$_2$CO), 3.74 (3H, s, OCH$_3$), 4.10 (2H, s, CH$_2$N), 6.7–7.8 (7H, m, Ar-H), 11.5 (1H, br-s, COOH).

Anal. Calc'd. for $C_{18}H_{21}NO_5S$: C, 59.49; H, 5.82; N, 3.84; S, 8.82. Found: C, 59.48; H, 5.68; N, 3.37; S, 9.22.

2-N-METHYLAMINOMETHYL-4-METHOXYPHENYLACETIC ACID (4a)

To a solution of liquid ammonia (300 ml.) was added 9.4 g. (0.026 mol.) of 3 at −50° C. and the mixture was stirred until a clear solution was obtained at the same temperature. To the solution was added 3.3 g. (0.14 g. atom) of Na in small pieces at −40° C. and the mixture was stirred for 2 hours. Ammonia was evaporated and the residue was dissolved in 100 ml. of water carefully. To the solution was added 100 ml. of Amberlite IR-C 50 (ammonium type) and the mixture was stirred for 30 minutes at room temperature. The resin was removed and the filtrate was treated with barium acetate until no more precipitate was observed. The precipitate was filtered off and the filtrate was chromatographed with a column of IR-120 ion-exchange resin (H$^+$, 100 ml.) by eluting with 5–10% ammonia. The eluate (2 L) containing the desired product was evaporated to dryness below 50° C. and the residue was triturated with acetone to give 4.4 g. (81%) of 4a, m.p. 225°–227° C.

ir: $\eta_{max}^{KBr}$ 1590, 1380, 1260, 1035 cm$^{-1}$.
nmr: $\delta_{ppm}^{D_2O}$ 2.77 (3H, s, N-CH$_3$), 3.6 (2H, s, CH$_2$CO), 3.87 (3H, s, OCH$_3$), 4.18 (2H, s, CH$_2$N), 6.8–7.4 (3H, m, phenyl-H).

2-N-METHYLAMINOMETHYL-4-HYDROXYPHENYLACETIC ACID (4b)

A mixture of 2.9 g. (0.014 mol.) of 4a in 30 ml. of 48% hydrobromic acid was refluxed for 5 hours and the solution was evaporated to dryness. The residue was dissolved in 50 ml. of water. The solution was chromatographed on a column of Amberlite IR-120 (H$^+$, 50 ml.) eluting with 5–10% ammonia. The eluate was collected in 250 ml. fractions. Fractions containing the product were combined and evaporated to dryness below 50° C. The residue was triturated with acetone to give 1.3 g. (48.5%) of 4b, which was crystallized from 80% ethanol. M.p. 218°–221° C.

ir: $\eta_{max}^{KBr}$ 2000–3400, 1610, 1540, 1460, 1380, 1270 cm$^{-1}$.
uv: $\lambda_{max}^{1\%K_2CO_3}$ 243 nm ($\epsilon$: 4700), 297 nm ($\epsilon$: 1350).
nmr: $\delta_{ppm}^{D_2O+NaOH}$ 2.64 (3H, s, N-CH$_3$), 3.47 (2H, s, CH$_2$CO), 3.94 (2H, s, N-CH$_2$), 6.5–7.2 (3H, m, phenyl-H).

Anal. Calc'd. for $C_{10}H_{13}NO_3$: C, 61.53; H, 6.71; N, 7.17. Found: C, 61.44; H, 6.81; N, 17.20.

2-N-T-BUTOXYCARBONYL-N-METHYLAMINOMETHYL-4-METHOXY-PHENYLACETIC ACID (5, R = CH$_3$)

A mixture of 1.05 g. (5 m.mol.) of 4a, 1.43 g. (6 m.mol.) of t-butyl 4,6-dimethylpyrimidin-2-ylthiolcarbonate and 1.4 ml. of triethylamine in 40 ml. of 50% THF was stirred at room temperature for 20 hours. Most of the THF was evaporated and the resulting aqueous solution (ca. 20 ml.) was washed with ether. The water layer was acidified with 6N HCl and extracted with ether (3 × 10 ml.). The ethereal extracts were washed with water (10 ml.) and a saturated aqueous NaCl solution (10 ml.), treated with a small amount of active carbon and dried over $Na_2SO_4$. The filtrate was evaporated to dryness to give 1.0 g. (77.5%) of 5 (R = CH$_3$) as an oil.

nmr: $\delta_{ppm}^{CDCl_3}$ 1.47 (9H, s, BOC-H), 2.77 (3H, s, N—CH$_3$), 3.60 (2H, s, CH$_2$CO), 3.79 (3H, s, O-CH$_3$), 4.49 (2H, s, CH$_2$N), 6.1–7.3 (3H, m, phenyl-H).

2-N-T-BUTOXYCARBONYL-N-METHYLAMINOMETHYL-4-HYDROXY-PHENYLACETIC ACID (5, R = H)

A mixture of 1 g. (4.78 m.mol.) of 4b, 1.5 g. (6.3 m.mol.) of t-butyl 4,6-dimethylpyrimidin-2-ylthiolcarbonate and 2.1 ml. of triethylamine in 50 ml. of 50% aqueous THF solution was stirred at room temperature for 20 hours. The mixture was concentrated to 20 ml. under reduced pressure. The concentrate was washed with ether (10 ml.), acidified with 6N HCl and extracted with ethyl acetate (2 × 100 ml.). The combined extracts were washed with water (30 ml.) and a saturated aqueous NaCl solution (2 × 30 ml.), treated with a small amount of active carbon and dried over anhydrous Na$_2$SO$_4$. The filtrate was evaporated to dryness to give 1.3 g. (92%) of 5 (R = H) as an oil.

ir: $\eta_{max}^{liq}$ 3000–3600, 1670, 1260, 1150 cm$^{-1}$.

nmr: $\delta_{ppm}^{CDCl_3}$ 1.44 (9H, s, C(CH$_3$)$_3$), 2.73 (3H, s, N—CH$_3$), 3.54 (2H, s, CH$_2$CO), 4.38 (2H, s, CH$_2$N), 6.5–7.3 (3H, m, phenyl-H).

PREPARATION OF ORTHO-N-METHYLAMINOMETHYL-PHENYLACETIC ACID.

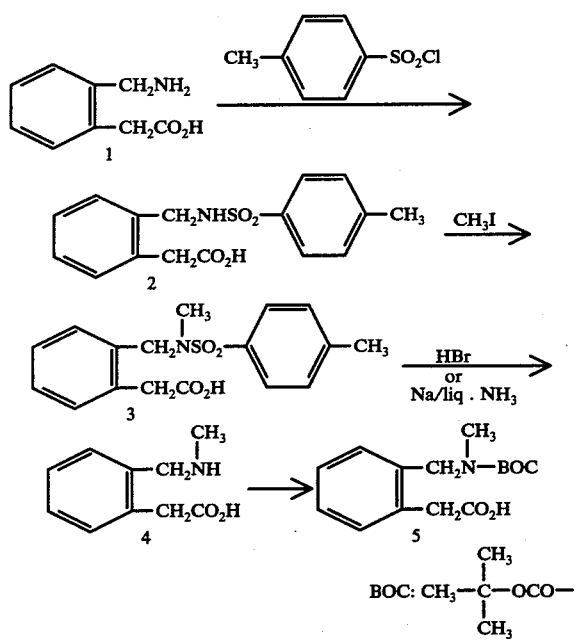

O-(P-TOLUENESULFONYLAMINOMETHYL)-PHENYLACETIC ACID (2)

To a stirred solution of o-aminomethylphenylacetic acid hydrochloride (7.50 g., 37 m.mol.) and sodium hydroxide (4.74 g., 118 m.mol.) in water (100 ml.) was added p-toluenesulfonyl chloride (7.64 g., 40 m.mol.) in portions at 60° C. The mixture was stirred for 1 hour at the same temperature and acidified with hydrochloric acid. The mixture was extracted with ethyl acetate (4 × 50 ml.). The combined extracts were washed with water, treated with a small amount of carbon and dried. The solvent was evaporated under reduced pressure and the residue crystallized from ethyl acetate to afford 2 as colorless prisms. Yield, 9.84 g. (84%). M.p. 155°–156° C.

ir: $\eta_{max}^{nuj}$ 3300, 1705, 1335, 1170 cm$^{-1}$.

nmr: $\delta_{ppm}^{DMSO-d_6}$ 2.38 (3H, s, CH$_3$), 3.65 (2H, s, CH$_2$CO), 3.97 (2H, d, J=5 Hz, CH$_2$N), 7.1–8.2 (9H, m, phenyl-H & NH).

Anal. Calc'd. for C$_{16}$H$_{17}$NO$_4$S: C, 60.17; H, 5.37; N, 4.39; S, 10.10. Found: C, 60.11, 60.15; H, 5.43, 5.40; N, 4.28, 4.30; S, 9.72, 9.80.

N-O-P-TOLUENESULFONYL-N-METHYLAMINOMETHYLPHENYLACETIC ACID (3)

A mixture of 2 (9.0 g., 28 m.mol.) sodium hydroxide (6.0 g.) and methyl iodide (6 ml.) in water (60 ml.) was heated in a sealed tube for 30 minutes at 70° C. After cooling, the reaction mixture was acidified with hydrochloric acid to separate pale yellow precipitate which was crystallized from ethyl acetate-n-hexane to give colorless prisms, 3. Yield, 8.5 g. (91%). M.p. 162°–163° C.

ir: $\eta_{max}^{KBr}$ 2700–2300, 1700, 1600, 1345, 1200, 925 cm$^{-1}$.

nmr: $\delta_{ppm}^{D_2O+KOH}$ 2.37 (3H, s, CH$_3$), 2.49 (3H, s, CH$_3$), 3.80 (2H, s, CH$_2$CO), 4.18 (2H, s, CH$_2$N), 7.0–8.0 (8H, m, phenyl-H).

Anal. Calc'd. for C$_{17}$H$_{19}$NO$_2$: C, 61.24; H, 5.74; N, 4.20; S, 9.61. Found: C, 61.31, 61.36; H, 5.73, 5.71; N, 4.51, 4.29; S, 9.63, 9.55.

N-METHYLAMINOMETHYLPHENYLACETIC ACID (4)

Method A (using hydrobromic acid) - A mixture of 28.6 g. (0.086 mol.) of 3 and 20 g. (0.213 mol.) of phenol in 260 ml. of 48% hydrobromic acid was refluxed for 30 minutes. The mixture was cooled, diluted with the same volume of water and washed with ethyl acetate (2 × 50 ml.). The aqueous layer was evaporated to dryness in diminished pressure to give an oil which was chromatographed on a column of Amberlite IR-120 (H$^+$ form, 200 ml.) eluting with 5% ammonium hydroxide solution. The eluate (2.5 l.) was collected and evaporated to dryness under reduced pressure. The residue was triturated with acetone and crystallized from ethanol to afford 6.7 g. (43.5%) of 4 as colorless needles, melting at 168°–170° C. (dec.).

Method B (using metallic sodium in liquid ammonia) - To a mixture of 3 (35 g., 0.105 mol.) in liquid ammonia (1000 ml.) was added 13.3 g. (0.578 atom) of sodium in small pieces under vigorous stirring over a period of 2 hours. The ammonia was evaporated with stirring on a water-bath in a well-ventilated hood and finally under reduced pressure to remove it completely. The residue was dissolved in ice water (400 ml.) and the solution was stirred with ion-exchange resin (H$^+$ form, 400 ml.) for 0.5 hour at room temperature. The resin was filtered off and to the filtrate was added an aqueous 1 M solution of barium acetate until no more precipitate was formed (ca 50 ml. of the barium acetate solution was required). The mixture was filtered and the filtrate was chromatographed on a column of IR-120 (H$^+$ form, 400 ml.) as in Method A to give 13.6 g. (72%) of 4.

O-(N-METHYL-N-T-BUTOXYCAR-BONYLAMINOMETHYL)PHENYLACETIC ACID (5)

t-Butyl 4,6-dimethylpyrimidin-2-ylthiolcarbonate (11 g., 0.048 mol.) was added in one portion to a mixture of 4 (7.2 g., 0.04 mol.) and 1,1,3,3-tetramethylguanidine (6.9 g., 0.06 mol.) in 50% aqueous THF and the mixture was stirred overnight at room temperature. The THF being evaporated under reduced pressure, the aqueous solution was acidified to pH 2 with dil. hydrochloric acid and extracted with ethyl acetate (2 × 20 ml.). The combined extracts were washed with water, treated with a small amount of active carbon and evaporated under diminished pressure. The residue was triturated with hexane and crystallized from n-hexane-ether to afford 9.2 g. (83%) of 5 as colorless prisms. M.p. 96°–98° C.

ir: $\eta_{max}^{KBr}$ 1730, 1630, 1430, 1830, 1250 cm$^{-1}$.

nmr: $\delta_{ppm}^{CDCl_3}$ 1.49 (9H, s, t-butyl), 2.78 (3H, s, N-CH$_3$), 3.72 (2H, s, CH$_2$CO), 4.25 (2H, s, CH$_2$N), 7.28 (4H, s, phenyl), 9.83 (1H, s, —COOH).

Anal. Calc'd. for $C_{15}H_{21}NO_4$: C, 64.50; H, 7.58; N, 5.01. Found: C, 64.69; H, 7.66; H, 4.89.

PREPARATION OF 3-N-METHYLAMINOMETHYL-2-THIENYLACETIC ACID

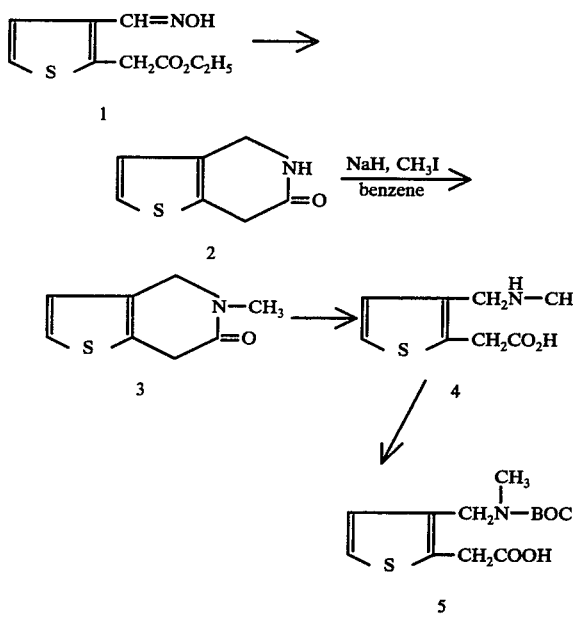

3-AMINOMETHYL-2-THIENYLACETIC ACID δ-LACTAM (2)

Glacial acetic acid (140 ml.) and added dropwise with stirring to a mixture of 2-ethoxycarbonylmethylthiophene-3-carboxaldehyde oxime (1) (41 g., 0.19 mole) and zinc dust (65.4 g., 1 mole) in methanol, and the mixture was stirred under reflux for 4 hours. The mixture was cooled and insolubles were removed by filtration and washed with methanol (3 × 50 ml.). The filtrate was combined with the washings and evaporated in vacuo to dryness, the residue being extracted with methanol (5 × 100 ml.). The methanol extracts were combined and evaporated under reduced pressure. To the residue was added water (50 ml.) and the mixture was adjusted to pH 10 with $Na_2CO_3$ and extracted with chloroform (3 × 100 ml.). The combined chloroform extracts were washed with water (10 ml.), dried over $MgSO_4$, and evaporated under reduced pressure. The residual oil (30 g.) was triturated with hot benzene (150 ml.). The colorless needles were collected by filtration and recrystallized from ethyl acetate to give the lactam 2 (7.7 g., 26%), melting at 195°–196° C.

UV: $\lambda_{max}^{MeOH}$ 232 nm ($\epsilon$, 6500)

Anal. Calc'd. for $C_7H_7NOS$: C, 54.88; H, 4.61; N, 9.14; S, 20.93. Found: C, 55.04; H, 4.45; N, 9.13; S, 20.50.

3-N-METHYLAMINOMETHYL-2-THIENYLACETIC ACID δ-LACTAM (3)

To a suspension of sodium hydride (50% in paraffin, 1.82 g., 38 m.moles) in absolute benzene (500 ml.) was added the lactam 2 (4.85 g., 32 m.moles) with stirring under nitrogen atmosphere and the mixture was refluxed for 2 hours. Methyl iodide (22.7 g., 160 m.moles) was added in one portion at room temperature and the mixture was again refluxed for 2 hours. Ice-water (50 g.) was added to the mixture and organic layer was separated. The aqueous layer was extracted successively with benzene (2 × 50 ml.) and chloroform (50 ml.). The extracts were combined and dried on $MgSO_4$. The solvent was evaporated under reduced pressure. To the residue was added a hot mixture of benzene-n-hexane (1:1, 100 ml.) to recover 2 as needles (2.02 g., 42%). The filtrate was evaporated and the residue was crystallized from benzene-n-hexane to afford colorless plates 3. Yield: 2.7 g. (51%). M.p. 98°–100° C.

ir: $\eta_{max}^{nujol}$ 1620 cm$^{-1}$.

nmr: $\delta_{max}^{CHCl_3}$ 3.15 (3H, s, N—CH$_3$), 3.72 (2H, t, J=3Hz, CH$_2$CO), 4.53 (2H, t, J=3Hz, —CH$_2$—N), 6.87 (1H, d, J=4.5Hz, thiophene-H$\beta$), 7.30 (1H, d, J=4.5 Hz, thiophene-H$\alpha$).

uv: $\lambda_{max}^{MeOH}$ 232 nm ($\epsilon$, 6700)

Anal. Calc'd. for $C_8H_9NOS$: C, 57.46; H, 5.42; N, 8.38; S, 19.17. Found: C, 57.56; H, 5.26; N, 8.31; S, 19.13.

3-(N-METHYLAMINOMETHYL)-2-THIENYLACETIC ACID (4)

A mixture of the lactam 3 (3.5 g., 21 m.moles) and 6N HCl (100 ml.) was heated under reflux for 12 hours. The mixture was treated with carbon and concentrated to dryness under reduced pressure. The residual oil was dissolved in water (10 ml.) and chromatographed on a column of IR-120 (H$^+$, 50 ml.). The column was eluted with water (200 ml.) and 5N NH$_4$OH (3 L.). The amino acid 4 (3.0 g., 77%) was isolated by evaporation of the ammonia eluates followed by crystallization from aqueous acetone. M.p. 181°–182° C.

ir: $\eta_{max}^{KBr}$ 1570, 1360 cm$^{-1}$.

nmr: $\delta_{ppm}^{D_2O}$ 2.21 (3H, s, N—CH$_3$), 3.80 (2H, s, CH$_2$CO), 4.20 (2H, s, CH$_2$—N), 7.19 (1H, d, J=6Hz, thiophene-H$\beta$), 7.46 (1H, d, J=6Hz, thiophene-H$\alpha$).

uv: $\lambda_{max}^{H_2O}$ 237 nm ($\epsilon$, 7600)

Anal. Calc'd. for $C_8H_{11}NO_2S$: C, 51.87; H, 5.99; N, 7.56; S, 17.31. Found: C, 51.67; H, 6.50; N, 7.28; S, 16.69.

3-(N-T-BUTOXYCARBONYL-N-METHYLAMINOMETHYL)-2-THIENYLACETIC ACID (5)

To a mixture of 3-N-methylaminomethyl-2-thienylacetic acid 4 (2.7 g., 14.6 m.moles) and triethylamine (6 g., 60 m.moles) in 50% aqueous acetone (60 ml.) was added dropwise t-butoxycarbonyl azide (4.2 g., 29.2 m.moles) over a period of 20 minutes at 0° C. with vigorous stirring. The reaction mixture was stirred overnight at room temperature and concentrated under reduced pressure. The concentrate was washed with ether (2 × 20 ml.), adjusted to pH 2 with concentrated HCl and extracted with ethyl acetate (2 × 50 ml.). The ethyl acetate extracts were washed with a saturated aqueous NaCl solution, dried on $MgSO_4$, treated with charcoal and evaporated under reduced pressure. The residue was triturated with n-hexane and crystallized from n-hexane-benzene to give 3.68 g. (88%) of colorless needles 5 melting at 82°–83° C.

ir: $\eta_{max}^{nujol}$ 1730, 1640 cm$^{-1}$.

nmr: $\delta_{ppm}^{CDCl_3}$ 1.47 (9H, s, BOC—H), 2.78 (3H, s, N—CH$_3$), 3.87 (2H, s, CH$_2$-CO), 4.48 (2H, s, CH$_2$-N), 6.91 (1H, d, J=6Hz, thiophene-H$\beta$), 7.20 (1H, d, J=6Hz, thiophene-H$\alpha$), 10.63 (1H, s, CO$_2$H, disappeared by addition of D$_2$O).

Anal. Calc'd. for $C_{13}H_{19}NO_4S$: C, 54.72; H, 6.71; N, 4.91; S, 11.24. Found: C, 54.91; H, 6.85; N, 4.92; S, 11.19.

1-CARBOXYPROPYL-2-MERCAPTOTETRAZOLE.

To a solution of 40.8 g. (0.63 mole) of sodium azide in 400 ml. of water at 60° C. was added 66.8 g. (0.42 mole) of methoxycarbonyl propyl isothiocyanate [D. L. Garmaise, et al., J. Amer. Chem. Soc., 80, 3332 (1958)] dropwise. The mixture was heated at 78° C. for 2 hours, cooled to room temperature and adjusted to pH 12 with 50% sodium hydroxide solution. The solution was then heated at reflux for 1½ hours, cooled to 27° C. and adjusted to pH 2 with 6N hydrochloric acid. The mixture was filtered through diatomaceous earth ("Dicalite") and the cake was washed with 100 ml. of ethyl acetate. The filtrate was extracted with 4 × 100 ml. of ethyl acetate. The extracts were combined, washed with water and dried by azeotropic distillation to precipitate an oil which crystallized on cooling in an ice-bath to yield 22 g. 1-carboxypropyl-2-mercaptotetrazole. The nmr spectrum was consistent for the structure.

7-AMINO-3-(1-CARBOXYPROPYLTETRAZOL-5-YLTHIOMETHYL)-3-CEPHEM-4-CARBOXYLIC ACID.

To a suspension of 22 g. (0.081 mole) of 7-aminocephalosporanic acid in 350 ml. of pH 6.4 0.1M phosphate buffer was added 16.9 g. (0.089 mole) of 1-carboxypropyl-5-mercaptotetrazole and 1.5 g. of sodium bisulfite. The mixture was heated under nitrogen to 55° C. and solid sodium bicarbonate was added until the solution became clear (pH 7.5). The solution was heated for 3.5 hours, cooled to 10° C. and adjusted to pH 2 with 6N hydrochloric acid. The precipitate was collected, washed with cold water and finally with methanol and air-dried to yield 17.5 g. of 7-amino-3-(1-carboxypropyltetrazol-5-ylthiomethyl)-3-cephem-4-carboxylic acid. The sample was recrystallized from 100 ml. of methanol with concentrated hydrochloric acid added dropwise until the solution was clear. The solution was adjusted to pH 5 with concentrated ammonium hydroxide and the precipitate was collected to yield 6.7 g. The nmr and ir spectra were consistent for the structure.

The use of an "en-amine" blocking group with a prospective 7-side chain containing a free amino group prior to acylation of a nucleus such as II herein is well known as from U.S. Pat. Nos. 3,223,141, 3,813,390, 3,813,391, 3,823,141 and Belgium Pat. No. 773,773.

SODIUM 2-[N-(1-CARBETHOXYPROPEN-2-YL)AMINOMETHYL]-1,4-CYCLOHEXADIENYL ACETATE (4)

To a stirred solution of 460 mg. (0.02 mole) of metallic sodium in 100 ml. of absolute EtOH was added 3.34 g. (0.02 mole) of 2-aminomethyl-1,4-cyclohexadienylacetic acid and 3.1 g. (0.024 mole of ethyl acetoacetate and the mixture was heated to reflux for 4 hours with stirring. The hot reaction mixture was filtered and the filtrate was allowed to keep cold overnight to give 2.0 g. of colorless needles 4 melting at 264° C. The additional product (3.3 g.) was obtained by concentration of the mother liquid. The total yield was 5.3 g. (88%).

IR: $\eta_{max}^{nuj}$ 3300, 1635, 1600, 1570, 1300, 1275, 1170, 1090 cm$^{-1}$.

NMR: $\delta_{ppm}^{D_2O}$ 1.23 (3H, t, 7Hz, CH$_2$C$\underline{H}_3$), 1.96 & 2.25 (3H, s, C=C—C$\underline{H}_3$, cis & trans), 2.70 (4H, s,

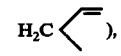

3.04 (2H, s, C$\underline{H}_2$CO), 3.66 & 3.95 (2H, s, C$\underline{H}_2$—N, cis & trans), 4.07 (2H, q, 7Hz, C$\underline{H}_2$CH$_3$), 4.45 & 4.56 (1H, s,

cis & trans), 5.76 (2H, s,

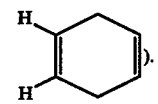

Anal. Calcd. for $C_{15}H_{20}NO_4Na$: C, 59.79; H, 6.69; N, 4.64. Found: C, 59.69; H, 6.76; N, 4.75.

2-T-BUTOXYCARBONYLAMINOMETHYL-4-HYDROXYPHENYLACETIC ACID is prepared, for example, according to U.S. Pat. No. 3,823,141.

o-(N-Methylaminomethyl)phenylacetic acid δ-lactam

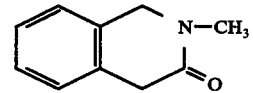

Sodium hydride (57% in paraffin, 4.3 g.; 0.11 mol.) was washed with dry n-hexane and suspended in dry benzene (100 ml.). To the suspension was added a solution of o-aminomethylphenylacetic acid δ-lactam (U.S. Pat. No. 3,796,716) (14.7 g., 0.1 mol.) in dry benzene or xylene (200 ml.) with stirring under a nitrogen atmosphere. The mixture was refluxed for one hour and cooled to room temperature. To the mixture was added methyl iodide (18 ml.) in one portion and the mixture was refluxed again for 1.5 hours. The reaction mixture was cooled to room temperature and poured into ice-water (100 ml.). The aqueous layer was separated from the organic layer and extracted with CHCl$_3$ (2 × 50 ml.). The extracts were combined with the organic layer and dried on MgSO$_4$. The solvent was removed and the oily residue was distilled in vacuo to afford 14.9 g. (92%) of o-(N-methylaminomethyl)phenylacetic acid δ-lactam, boiling at 130°–135° C/2 mmHg., m.p. 35°–37° C.

ir: $\eta_{max}^{KBr}$ 3300, 1620, 1490 cm$^{-1}$.

nmr: $\delta_{ppm}^{CDCl_3}$ 3.12 (3H, s), 3.59 (2H, t, J=1.5 Hz), 4.48 (2H, t, J=1.5 Hz), 7.21 (4H, br-s).

Anal. Calc'd. for $C_{10}H_{11}NO.\frac{1}{4}H_2O$: C, 72.49; H, 6.84; N, 8.45. Found: C, 72.78, 72.70; H, 6.76, 6.81; N, 8.49, 8.51.

O-N-METHYLAMINOMETHYLPHENYLACETIC ACID

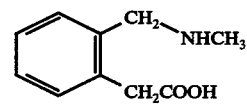

A mixture of the above-produced o-(N-methylaminomethyl)phenylacetic acid δ-lactam (5.0 g., 0.031 mol) and conc hydrochloric acid (500 ml.) was refluxed for 40 hours. The mixture was evaporated under reduced pressure, and the residual oil was dissolved in water (20 ml.) and treated with a small amount of active carbon. The filtrate was washed with benzene (50 ml.) and evaporated to dryness. The residual oil was crystallized by trituration with THF (or acetone) to give colorless needles of o-N-methylaminomethyl-phenylacetic acid hydrochloride (4.5 g., 67%). Anal. Calc'd. for $C_{10}H_{13}NO_2 \cdot HCl$: C, 55.69; H, 6.54; N, 6.49; Cl, 16.44. Found: C, 55.65, 55.74; H, 6.62, 6.60; N, 6.53, 6.53; Cl, 16.36.

Some unreacted starting material was recovered from the benzene layer and the THF washings (1.2 g., 24%, b.p. 140°–143° C/2mmHg).

An aqueous solution of o-N-methylaminomethyl-phenylacetic acid hydrochloride (5 g.) was column chromatographed with IR-120 ion-exchange resin ($H^+$, 70 ml.) and eluted with 3N $NH_4OH$ (2 l) to afford 3.9 g. (93%) of o-N-methylaminomethylphenylacetic acid as needles.

ir: $\eta_{max}^{KBr}$ 1650, 1470 $cm^{-1}$.

The following examples are given in illustration of, but not in limitation of, the present invention. All temperatures are in degrees Centigrade. 7-Aminocephalosporanic acid is abbreviated as 7-ACA; -ACA represents the moiety having the structure

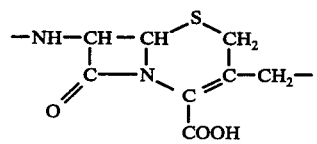

and thus 7-ACA can be represented as

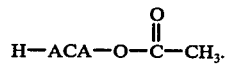

Methyl isobutyl ketone is represented as MIBK. "Skellysolve B" is a petroleum ether fraction of B.P. 60°–68° C. consisting essentially of n-hexane.

LA-1 resin is a mixture of secondary amines wherein each secondary amine has the formula

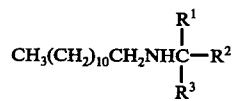

wherein each of $R^1$, $R^2$ and $R^3$ is a monovalent aliphatic hydrocarbon radical and wherein $R^1$, $R^2$ and $R^3$ contain in the aggregate from eleven to fourteen carbon atoms. This particular mixture of secondary amines, which is sometimes referred to in these examples as "Liquid Amine Mixture No. II," is a clear amber liquid having the following physical characteristics: viscosity at 25° C. of 70 cpd., specific gravity at 20° C. of 0.826; refractive index at 25° C. of 1.4554; distillation range at 10 mm., up to 170° C. - 0.5%, 170°–220° C. - 3%, 220°–230° C. - 90% and above 230° C. - 6.5%.

IR-120 is also called Amberlite IR-120 and is a strong cation exchange resin containing sulfonic acid radicals. Amberlite IR-120 is a commercially available cation exchange resin of the polystyrene sulfonic acid type; it is thus a nuclear sulfonated polystyrene resin cross-lined with divinyl benzene obtained by the procedure given by Kunin, Ion Exchange Resins, 2nd. Edition (1958), John Wiley and Sons, Inc. Therein see pages 84 and 87 for example.

Amberlite IRC-50 is a commercially available cation exchange resin of the carboxylic type; it is a copolymer of methacrylic acid and divinylbenzene.

Dicyclohexylcarbodiimide is abbreviated as DCC, tetrahydrofuran as THF, thin layer chromatography as TLC, p-toluenesulfonyl as Ts and methanol as MeOH.

When the following instrumental readings are given, for infrared upsilon if used is written $\eta$, for ultraviolet lambda is written as $\lambda$, with molar absorptivity as epsilon ($\epsilon$) and for nuclear magnetic resonance (nmr) delta is written as $\delta$ and tau as $\tau$ ($\delta$ = 10- ).

DESCRIPTION OF THE PREFERRED EMBODIMENTS

EXAMPLE 1

7-(2-Aminomethylphenylacetamido)-3-(1-carboxymethyltetrazol-5-ylthiomethyl)-3-cephem-4-carboxylic acid

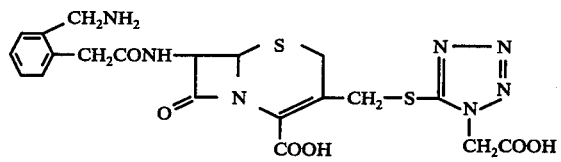

1. Into a 3 necked flask containing 100 ml. of deionized water and set up with an agitator and thermometer, add 7.6 grams (0.021 mole) of 7-amino-3-(1-carboxymethyltetrazol-5-ylthiomethyl)-3-cephem-4-carboxylic acid and 3.4 grams (0.034 mole) of N-methylmorpholine. Cool to 0° C. With agitation, the solution is maintained at 0° C. using an ice bath.

2. In a separate flask set up with an agitator, add 9.6 grams (0.03 mole) of sodium 2-(1-methoxycarbonyl-1-propen-2-ylaminomethyl)phenylacetate and 184 ml. of tetrahydrofuran. With agitation, the suspension is cooled to $-30°$ C., using a dry ice acetone bath. Maintaining agitation and temperature at $-30°$ C., add 20 drops of dimethylbenzylamine and 4.4 grams (0.03 mole) of isobutyl chloroformate. Stir the resulting mixture for 5 minutes.

3. Add all of the mixture from step 2 to the agitation solution in step 1 at one time. The resulting solution is maintained at 3° C. with agitation for 1 hour.

4. Evaporate the tetrahydrofuran from the reaction mixture at 30° C. using vacuum (15 mm).

5. Adjust the pH of the remaining aqueous solution to 4.0 using concentrated hydrochloric acid.

6. Add 2.5 grams of charcoal ("Darco G-60") to the solution and mix for 20 minutes. Remove the carbon by filtration.

7. The filtrate is layered with 120 ml. of ethyl acetate and with agitation the pH is lowered to 3.8 with concentrated hydrochloric acid. Some light tan colored solids may separate and are removed by filtration. (Save for reworking and recovery).

8. Using an ice bath, the filtrate is cooled to 5° C. and with agitation the pH is lowered to 2.5 – 2.8 with concentrated hydrochloric acid. Maintain the temperature at 5° C. and continue agitation for 1 hour.

9. Collect the product by filtration. Wash the filter cake with 5 ml. of cold deionized water followed by 5 ml. of cold methanol.

10. Air dry the solid 7-(2-aminomethylphenylacetamido)-3-(1-carboxymethyltetrazol-5-ylthiomethyl)-3-cephem-4-carboxylic acid to constant weight. (A typical run produced 4.1 grams of product).

11. The product as obtained from step 10 is passed through a 200 mesh stainless steel screen.

12. Ten grams of this 200 mesh product is slurried in 100 ml. of chloroform. Five ml. of triethylamine is added and the mixture is heated to 50° C. with rapid stirring. The mixture is slurried at 50° C. for 5 minutes.

13. The mixture is filtered hot (7-ACA, 7-amino-3-(1-carboxymethyltetrazol-5-ylthiomethyl)-3-cephem-4-carboxylic acid, pigments and other impurities are soluble in the hot chloroformtriethylamine solution). The filter cake is washed with 25 ml. of chloroform and air dried for 2 hours. Yield: 1-8 grams of 7-(2-aminomethylphenylacetamido)-3-(1-carboxymethyltetrazol-5-ylthiomethyl)-3-cephem-4-carboxylic acid.

14. The product as obtained for step 13 is passed through a 200 mesh screen.

15. Ten grams of this 200 mesh product is slurried in 75 ml. of 0.1 N hydrochloric acid for 10 – 15 minutes. The mixture is filtered and the filter cake is washed with 25 ml. of water, 50 ml. of methanol, and air dired at room temperature for 2–3 hours. Yield: Up to 10 g. is obtained.

16. Ten grams of 7-(2-aminomethylphenylacetamido)-3-(1-carboxymethyltetrazol-5-ylthiomethyl)-3-cephem-4-carboxylic acid as obtained from step 15 is slurried in 65 ml. of methanol.
  (a) Two ml. of concentrated hydrochloric acid is added. A solution or near solution is obtained. Stir for 5 minutes.
  (b) One hundred and 30 ml. of water is rapidly added with vigorous stirring to the solution of a) above. An instantaneous precipitate (containing most of the color) is obtained. (A pH of 1.3 to 1.6 is required.)
  (c) The mixture is slurried for 1 minute and rapidly filtered. (Save solids for rework and recovery.)
  (d) The filtrate is seeded and moderately stirred. The onset of crystallization is about 15–30 minutes.
  (e) The mixture is stirred at ambient room temperature or at 4° C. for 2 hours after the onset of crystallization.
  (f) The crystals are removed by filtration, washed with 25 ml. of 65% water, 35% methanol mixture (v/v), 50 ml. of methanol, and vacuum dried at 50° C. for 24 hours. Yield: Up to 9 grams of purified, white 7-(2-aminomethylphenylacetamido)-3-(1-carboxymethyltetrazol-5-ylthiomethyl)-3-cephem-4-carboxylic acid is obtained.

17. The following are two alternate procedures for the crystallization of 7-(2aminomethylphenylacetamido)-3-(1-carboxymethyltetrazol-5-ylthiomethyl)-3-cephem-4-carboxylic acid (A)
1. Ten grams of product as obtained from step 15 is slurried in 100 ml. of methanol.

2. Two ml. of concentrated hydrochloric acid is added and a solution or near solution is obtained.

3. One and five tenths gram of charcoal ("Darco G-60") is added and the mixture is slurried for 0.5 hour.

4. The carbon is removed by filtration and washed with 20 ml. of methanol. The methanol wash is added to the filtrate.

5. One hundred and twenty ml. of water is added to the filtrate. (A small amount of precipitate may come out. This is removed by filtration and saved for rework-recovery.)

6. The solution of step 5 is rapidly stirred and adjusted to pH 2.5 – 3.0 with 10% sodium hydroxide. Crystals form.

7. The mixture is slurried for 0.5 hour. The crystals are removed by filtration, washed with 20 ml. of 50% methanol-water (v/v), 30 ml. of methanol and vacuum dried at 50° C. for 24 hours. Yield: Up to 9 grams of purified 7-(2-aminomethylphenylacetamido)-3-(1-carboxymethyltetrazol-5-ylthiomethyl)-3-cephem-4-carboxylic acid is obtained.

(B)
1. Ten grams of product as obtained from step 15 is slurried in 75 ml. of water.

2. Ten percent sodium hydroxide is added to a maintained pH of 6.8 – 7.2. A solution or partial solution may be obtained.

3. One and five tenths grams of charcoal ("Darco G-60") is added and the mixture is slurried for 0.5 hour at a maintained pH of 6.8 – 7.2 (continued addition of 0.1 to 1 N sodium hydroxide).

4. The carbon is removed by filtration. The carbon is washed with 20 ml. of water which is added to the filtrate.

5. The pH 6.8–7.2 solution of step 4 may be crystallized at pH 2.5—3.0 as described in steps 6 and 7 of A, above or at pH 1.2–1.5 (by addition of hydrochloric acid) and as described in d, e, and f of step 16. In both instances, up to 9 grams of crystalline 7-(2-aminomethylphenylacetamido)-3-(1-carboxymethyltetrazol-5-ylthiomethyl)-3-cephem-4-carboxylic acid is obtained. This product is frequently obtained as a crystalline monohydrate.

EXAMPLE 2

7-(2-Aminomethyl-1,4-cyclohexadienylacetamido)-3-(1-carboxymethyltetrazol-5-ylthiomethyl)-3-cephem-4-carboxylic acid.

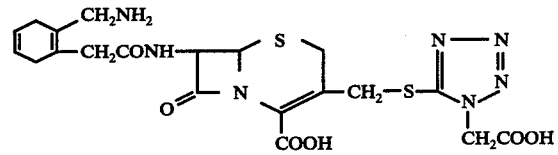

A solution of 0.80 g. (0.003 mole) of 2-t-butoxycarbonylaminomethyl-1,4-cyclohexadienylacetic acid and 0.303 g. (0.003 mole) of triethylamine in 19.2 ml. of THF was stirred at 0° and 0.41 g. (0.003 mole) of isobutyl chloroformate was added. The mixture was stirred for 30 min. at 0° and added to a solution of 0.003 mole of 7-amino-3-(1-carboxymethyltetrazol-5-ylthiomethyl)-3-cephem-4-carboxylic acid and 0.61 g. (0.006 mole) of TEA in 9.2 ml. of 50% THF. The resulting solution was stirred for 1½ hr. at 25°. The tetrahydrofuran was evaporated at 30° at 15 mm and the residue was washed 2 × 30 with ether and then diluted in half with water. The solution was acidified to pH 3.5 with dilute hydrochloric acid and the product was collected, dried for 18 hr. in vacuo over $P_2O_5$ at 25° to yield 1.55 g.

(54.0%) of white powder. A total of 3.4 ml. of trifluoroacetic acid was added to the above 7-(2-t-butoxycarbonylaminomethyl-1,4-cyclohexadienylacetamido)-3-(1-carboxymethyltetrazol-5-ylthiomethyl)-3-cephem-4-carboxylic acid and stirred for 1 hr. at 0°. The solution was diluted with 150 ml. ether and the precipitate was collected by filtration. The trifluoroacetate salt was suspended in 3.4 ml. of water and adjusted to pH 4.5 with dilute ammonium hydroxide. The gummy residue was triturated with water, collected and washed with water and acetone. The product was dried 18 hr. in vacuo over $P_2O_5$ at 25° to yield 53 mg. (15.72%) 7-(2-aminomethyl-1,4-cyclohexadienylacetamido)-3-(1-carboxymethyltetrazol-5-ylthiomethyl)-3-cephem-4-carboxylic acid; m.p. > 160°, slow decomp.

Anal. Calcd. for $C_{20}H_{23}N_7O_6S_2 \cdot \frac{1}{2} H_2O$; C, 45.18; H, 4.55; N, 18.44. Found: C, 45.46; H, 4.68; N, 17.09. The IR and NMR spectra were consistent for the structure.

Samples of the compounds prepared in Examples 1 and 2 after solution in water and dilution with Nutrient Broth were found to exhibit the following Minimum Inhibitory Concentrations (M.I.C.) in mcg./ml. versus the indicated microorganisms as determined by overnight incubation at 37° C. by Tube Dilution.

3. Two grams of activated charcoal ("Darco G-60") is added and the mixture is slurried for 0.5 hours. The pH is maintained at 7.4–7.7 with 1 N sodium hydroxide.

4. The carbon is removed by filtration and washed with 10 ml. of water. The wash is added to the filtrate.

5. The pH 7.4–7.7 solution of step 4 is made sterile and pyrogen-free by suitable aseptic filtration and techniques.

The combined time required for completion of steps 3, 4 and 5 should not exceed 5 hours at ambient room temperature.

6. Using sterile technique, an approximate equal volume (65 ml.) of sterile, pyrogen-free acetone is added to the rapidly stirring sterile solution of step 5 over a 5 minute period.

7. Based upon the approximate original aqueous volume, an additional 2 volumes (120 ml.) of sterile, pyrogen-free acetone is added with rapid stirring over 15–20 minutes. Crystals form.

8. The mixture is slurried for 10 minutes.

9. An additional 3 volumes (180 ml.) of sterile acetone is added over a 15 minute interval. The mixture is slurried for 0.5 hour.

10. The crystals are collected by filtration, washed

|  | In Vitro Antibacterial Activity M.I.C. (μg./ml.) | | |
|---|---|---|---|
| Organisms | | Ex. 1 (soluble at ≧250 mg/ml as Na+ salt) | Ex. 2 |
| Str. pneumoniae* ($10^{-3}$)** | A9585 | 0.13 | 0.06 |
| Str. pyogenes* ($10^{-3}$) | A9604 | 0.13 | 0.13 |
| S. aureus Smith ($10^{-4}$) | A9537 | 1 | 0.5 |
| S. aureus-50% serum ($10^{-4}$) | A9537 | 4 | >0.5 |
| S. aureus BX1633 ($10^{-3}$) | A9606 | 1 | 1.3 |
| S. aureus BX1633 ($10^{-2}$) | A9606 | 2 | 2.5 |
| S. aureus Meth-Res ($10^{-3}$) | A15097 | 4 | 4 |
| Sal. enteritidis ($10^{-4}$) | A9531 | 0.06 | 0.16 |
| E. coli Juhl ($10^{-4}$) | A15119 | 0.5 | 1.3 |
| E. coli ($10^{-4}$) | A9675 | 16 | 16 |
| K. pneumoniae ($10^{-4}$) | A9977 | 0.13 | 0.3 |
| K. pneumoniae ($10^{-4}$) | A15130 | 2 | 2 |
| Pr. mirabilis ($10^{-4}$) | A9900 | 0.13 | 0.3 |
| Pr. morganii ($10^{-4}$) | A15153 | 32 | 8 |
| Ps. aeruginosa ($10^{-4}$) | A9843A | >125 | >125 |
| Ser. marcescens ($10^{-4}$) | A20019 | 125 | >125 |
| Ent. cloacae ($10^{-4}$) | A9656 | >125 | >125 |
| Ent. cloacae ($10^{-4}$) | A9657 | 0.25 | 0.3 |
| Ent. cloacae ($10^{-4}$) | A9659 | 32 | 32 |

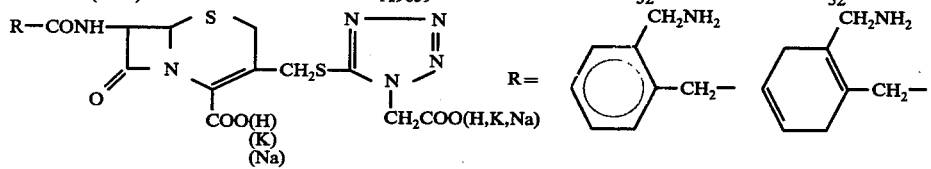

*45% Antibiotic Assay Broth + 50% Nutrient Broth + 5% serum
**Dilution of overnight broth culture

EXAMPLE 3

Trihydrate of Monosodium Salt of 7-(2-Aminomethylphenylacetamido)-3-(1-carboxymethyltetrazol-5-ylthiomethyl)-3-cephem-4-carboxylic acid 1. Ten grams of crystalline 7-(2-aminomethylphenylacetamido)-3-(1-carboxymethyltetrazol-5-ylthiomethyl)-3-cephem-4-carboxylic acid (as described and prepared in Example 1) is suspended in 50 ml. of deionized water.

2. Ten percent sodium hydroxide is slowly added with rapid stirring to a maintained or constant pH of 7.4–7.7. A solution or near solution is obtained.

with 75 ml. of sterile acetone and vacuum dried at 45°–50° C. or air dried at 50°–56° C. for 24 hours. Yield: Approximately 8.8 grams.

Properties of trihydrate of monosodium salt of 7-(2-aminomethylphenylacetamido)-3-(1-carboxymethyltetrazol-5-ylthiomethyl)-3-cephem-4-carboxylic acid:

% Water (KF) = 9.2 (theory = 9.05%)
% Sodium (flame photometer) = 4.0 (theory = 3.86%)
Solubility in water = > 500 mg./ml.
Stability in water = Stable for at least 24 hours at room temperature at 250 mg./ml.

FORMULATION OF INJECTABLE PRODUCTS

In situ preparation of monosodium salt of 7-(2-aminomethylphenylacetamido)-3-(1-carboxymethyltetrazol-5-ylthiomethyl)-3-cephem-4-carboxylic acid:

(A) 2.5 grams of 7-(2-aminomethylphenylacetamido)-3-(1-carboxymethyltetrazol-5-ylthiomethyl)-3-cephem-4-carboxylic acid (zwitterion) is suspended in 8.5 ml. of water with rapid stirring, sodium citrate or $Na_2HPO_4$ or $Na_3PO_4$ or other suitable "bases" are added until a solution is obtained (the pH should not be over 7.8). The amount of added "base" is noted.

(B) A physical mixture of 2.5 grams of 7-(2-aminomethylphenylacetamido)-3-(1-carboxymethyltetrazol-5-ylthiomethyl)-3-cephem-4-carboxylic acid and the solid "base" in proportions determined in "A" above is made. The later addition of water to obtain various concentrations of 7-(2-aminomethylphenylacetamido)-3-(1-carboxymethyltetrazol-5-ylthiomethyl)-3-cephem-4-carboxylic acid gives a solution of in situ prepared monosodium salt of 7-(2-aminomethylphenylacetamido)-3-(1-carboxymethyltetrazol-5-ylthiomethyl)-3-cephem-4-carboxylic acid.

This procedure may be desirable as trihydrate of monosodium salt of 7-(2-aminomethylphenylacetamido)-3-(1-carboxymethyltetrazol-5-ylthiomethyl)-3-cephem-4-carboxylic acid is not as stable at elevated temperatures as is the free-acid 7-(2-aminomethylphenylacetamido)-3-(1-carboxymethyltetrazol-5-ylthiomethyl)-3-cephem-4-carboxylic acid (zwitterion) monohydrate.

With regard to the stability of 7-(o-aminomethylphenylacetamido)-3-(1-methyl-1,2,3,4-tetrazol-5-ylthiomethyl)-3-cephem-4-carboxylic acid solutions at room temperature and at pH 10.3 (the lowest pH able to dissolve 150 mg./ml.) an almost instantaneous 50% loss of bioactivity is noted. An additional 21% activity is lost in the next 30 minutes.

By contrast, a solution containing 125.0 mg./ml. of the trihydrate of monsodium salt of 7-(2-aminomethylphenylacetamido)-3-(1-carboxymethyltetrazol-5-ylthiomethyl)-3-cephem-4-carboxylic acid at pH 7.0 showed no significant loss at room temperature for at least 24 hours.

The compound entitled 7-(o-aminomethylphenylacetamido)-3-(1-methyl-1,2,3,4-tetrazol-5-ylthiomethyl)-3-cephem-4-carboxylic acid of example 1 and claim 2 of U.S. Pat. No. 3,766,175 is a very potent cephalosporin exhibiting a highly desirable spectrum of activity particularly against certain Gram-negative organisms. Unfortunately, this zwitterion exhibits quite a low solubility in water and particularly in the blood stream which means at about pH 7.2 or thereabouts. To be more specific, attempts to measure this solubility gave results in the range of about 1.0–3.0 mg./ml. in both buffered aqueous media and in dog urine at room temperature. The pH of fresh beagle dog urine is 7.6. This raises a question as to the possible toxic effect in man of the administration of this zwitterion because of the fact that it is assumed that it will precipitate in crystalline form in the kidneys as it is concentrated therein during excretion. This, in man, would be highly undesirable. Conventional attempts to solve this prospective problem by the use of ordinary water soluble forms and derivatives of 7-(o-aminomethylphenylacetamido)-3-(1-methyl-1,2,3,4-tetrazol-5-ylthiomethyl)-3-cephem-4-carboxylic acid have proven unsuccessful because of conversion in the body of the salt or derivative to the zwitterion which then exhibits its natural low solubility in aqueous media and the blood. It was an objective of the present invention to solve this problem without loss of the valuable biological activity of 7-(o-aminomethylphenylacetamido)-3-(1-methyl-1,2,3,4-tetrazol-5-ylthiomethyl)-3-cephem-4-carboxylic acid. After various failures the problem was solved by the provision according to the present invention of 7-(2-aminomethylphenylacetamido)-3-(1-carboxymethyltetrazol-5-ylthiomethyl)-3-cephem-4-carboxylic acid which has the desired properties. To be more specific a sample of 7-(2-aminomethylphenylacetamido)-3-(1-carboxymethyltetrazol-5-ylthiomethyl)-3-cephem-4-carboxylic acid in pH 7.0 phosphate buffer at 25° C. exhibited a solubility in mg./ml. greater than 15.3 and less than 13.6; in this instance the capacity of the buffer was not sufficient and the pH dropped to 6.48. Thus the 7-(2-aminomethylphenylacetamido)-3-(1-carboxymethyltetrazol-5-ylthiomethyl)-3-cephem-4-carboxylic acid provided by the present invention even in its zwitterionic form is too soluble in the blood stream to crystallize in the kidneys and thereby cause fear of toxic results in at least some patients.

In addition, as set forth above the combination of the lack of aqueous solubility presented a problem which was solved by the preparation of the trihydrate of monosodium salt of 7-(2-aminomethylphenylacetamido)-3-(1-carboxymethyltetrazol-5-ylthiomethyl)-3-cephem-4-carboxylic acid of the present invention which exhibits such solubility at pH's suitable for injection in man such as about pH 7 and still exhibits satisfactory solubility in the blood stream and the fluids in the kidney even if converted in the body to the zwitterionic form.

EXAMPLE 4

7-(2-aminomethyl-1,4-cyclohexadienylacetamido)-3-(1-carboxyethyltetrazol-5-ylthiomethyl)-3-cephem-4-carboxylic acid Substitution in the procedure of example 2 for the 7-amino-3-(1-carboxymethyltetrazol-5-yl-thiomethyl)-3-cephem-4-carboxylic acid used therein of 7-amino-3-(1-carboxymethyltetrazol-5-ylthiomethyl)-3-cephem-4-carboxylic acid produces the title compound.

EXAMPLE 5

7-(3-aminomethyl-2-thienylacetamido)-3-(1-carboxymethyltetrazol-5-ylthiomethyl)-3-cephem-4-carboxylic acid (A) 7-(3-t-butoxycarbonylaminomethyl-2-thienylacetamido)-3-(1-carboxymethyltetrazol-5-ylthiomethyl)-3-cephem-4-carboxylic acid A mixture of 3-t-butoxycarbonyl-aminomethyl-2-thienyl acetic acid (542 mg., 2 mmoles), 2,4-dinitrophenol (368 mg., 2 mmoles) and dicyclohexylcarbodiimide (412 mg., 2 mmoles) in tetrahydrofuran (THF) was stirred at room temperature for 1.5 hrs. The precipitated urea was removed and the filtrate was evaporated under reduced pressure. The resulting active ester (1.0 g.) was dissolved in 10 ml. of THF and added to a mixture of 7-amino-3-(1-carboxymethyl or tetrazol-5-ylthiomethyl-3-cephem-4-carboxylic acid (656 mg., 2 m. moles) and triethylamine (816 mg., 8 m. moles) in water (5 ml.) at 0° C with stirring. Stirring was continued for 3.5 hrs. at room temperature and the reaction mixture was added to water (20 ml. and washed with ether (4 × 20 ml.). The aqueous solution was layered with ethyl acetate and adjusted to pH 2 withconc. HCl at 5° C.

The organic layer was separated and the aqueous layer extracted with ethyl acetate (2 × 50 ml.). The ethyl acetate extracts were combined, washed with saturated aqueous sodium chloride, dried over $HgSO_4$ and evaporated under reduced pressure. The residual oil was chromatographed on silica gel (10 g.). The column was developed successively with chloroform (150 ml.) and 3% methanol-chloroform (100 ml.). From the chloroform eluate 2,4-dinitrophenol (50 mg.) was recovered and the title cephalosporin was isolated by evaporation of the methanol-chloroform eluate.

Yield: 29%; m.p. 185°–188° C with decomposition. Anal. Calc'd. for $C_{23}H_{27}N_7O_8S_3$: C, 42.91; H, 4.54; N, 15.23; S, 14.94. Found: C 43.02; H, 4.17; N, 15.07; S, 15.04.

(B) 7-(3-Aminomethyl-2-thienylacetamido)-3-(1-carboxymethyltetrazol-5-ylthiomethyl)-3-cephem-4-carboxylic acid Trifluroracetic acid (0.6 ml.) was added to the blocked cephalosporin obtained in step A (610 mg., 1.05 m.moles) and 0° C and the mixture stirred at room temperature for 15 mins. To the reaction mixture was added anhydrous ether (15 ml.) to separate precipitate, which was collected by filtration, washed with anhydrous ether (2 × 10 ml.) and dissolved in acetonitrile (10 ml.). To the solution was added 2 drops of conc. ammonium hydroxide. The separated solid was collected by filtration, washed with acetonitrile (2 × 10 ml.) and dried at 75° C/1 mmHg for 7 hrs. to afford the title product, which was collected as the monoammonium salt after treatment with one equivalent of ammonium hydroide.

Yield: 83%; m.p. 174°–178° C with decomposition. Anal. Calc'd. for $C_{18}H_{21}N_8O_6S_3.H_2O$: C, 38.56; H, 4.32; N, 19.98; S, 17.16. Found: C, 38.89; H, 4.06; N, 18.83; S, 15.24. The IR and NMR were consistent with the structure.

EXAMPLE 6

7-(3-aminomethyl-2-thienylacetamido)-3-(1-carboxyethyltetrazol-5-ylthiomethyl)-3-cephem-4-carboxylic acid Substitution in the procedure of example 5 for the 7-amino-3-(1-carboxymethyltetrazol-5-ylthiomethyl)-3-cephem-4-carboxylic acid used therein of an equimolar quantity of 7-amino-3-(1-carboxyethyltetrazol-5-ylthiomethyl)-3-cephem-4-carboxylic acid produces the title compound.

EXAMPLE 7

7-(2-aminomethylphenylacetamido)-3-(1-carboxyethyltetrazol-5-ylthiomethyl)-3-cephem-4-carboxylic acid (A) Potassium-O-(1-carbomethoxy-propen-2-ylaminomethyl)-phenylacetate (Enamine).

1. Put 1000 g. of o-aminomethylphenylacetic acid, 340 g. of potassium hydroxide, 1412 g. of methyl acetoacetate and 32,400 ml. of absolute methanol into a tank.[1]

2. Heat the mixture to reflux for 4 hours while stirring.

3. Concentrate the reaction solution under reduced pressure at <50° C. to about 1/5 of the starting volume.[2]

4. Add 10,000 ml. of MIBK to the concentrate and continue the concentration at reduced pressure until the methanol is removed.

5. Add 10,000 ml. of MIBK or any amount necessary to make a workable slurry of the concentrate.

6. Stir and cool the mixture to 5°–10° C. for 30 minutes.

7. Filter the slurry and wash the cake with 5000 ml. of MIBK and then 5000 ml. of acetone.[3]

8. Dry the product in an air circulating oven at ∼40° C.

9. The yield is 1605–1680 g. or 88–92% of white crystalline product. MP = 140°–142° C.

(B) 7-(2-Aminomethylphenylacetamide)-3-(1-carboxyethyltetrazol-5-yl-thiomethyl)-3-cephem-4-carboxylic acid (A¹) Enamine (4.09 g.) from step A and 90 ml. of tetrahydrofuran were mixed in a 3-neck flask equipped with a stirrer, drying tube and cooled in a dry-ice acetone bath. Eight drops of N,N-dimethylbenzylamine was added and the mixture was cooled to −38° C. Isobutylchloroformate (1.95 g.) was added and stirred for 15 minutes.

(B¹) 7-amino-3-(1-carboxyethyltetrazol-5-ylthiomethyl)-3-cephem-4-carboxylic acid (3.5 g.) was dissolved in 50 ml. of water and 2.29 g. of N-methylmorpholine and cooled to 2° C. The anhydride from step A¹ was added to the solution with stirring. The mixture was stirred for 1.5 hours at 2° C. The tetrahydrofuran was removed in vacuo, the remainder layered with ethyl acetate and adjusted to pH 3. After stirring in an ice bath, the product was collected; 250 mg. M.P. 140 c̄ decomposition.

The IR and NMR were consistent with the title product, but indicated about 20% impurities, primarily starting material. When this compound was administered intramuscularly by injection at a dose of 10 mg./kg. of body weight in mice, a blood level of 22.3 mg./ml. was obtained at 15 minutes.

EXAMPLE 8

Laboratory Preparation of Sterile Monosodium BL-S786 Dihydrate

1. Suspend 10 grams of crystalline BL-S786 free acid in 100 ml. of 50% acetone-deionized water (v/v) at ambient room temperature (20°–23° C.).

2. Slowly add aqueous 40% sodium hydroxide with very rapid stirring to a maintained or constant pH of 7.4–7.7. A solution or near solution is obtained.

3. Add 1.5 grams activated charcoal (Darco G-60). Slurry for 0.5 hour.

4. Remove the carbon by filtration (positive pressure is preferred to avoid evaporation of acetone).

5. Wash the carbon filter cake with 15 ml. of 50% acetone-deionized water. Add the wash to the filtrate.

6. Pass the combined wash and filtrate through suitable sterilizing filters (positive pressure is preferred to avoid evaporation of acetone) to remove particles, pyrogens and bacteria. Collect the filtrate into a suitable sterile tank. The combined time required for completion of steps 2 through 6 inclusive, should not exceed 5 hours at ambient room temperatures (20°–23° C.).

7. Maintaining rapid agitation and using sterile technique, add 55 ml. sterile, pyrogen-free acetone over a 30-minute interval to the sterile solution of step 6. Crystals start to form after most or all of the acetone has been added. Stir for an additional 0.5 hour to build up a crystalline mass.

8. Continue the rapid agitation and add 80–85 ml. sterile, pyrogen-free acetone over a 1 hour interval. Stir an additional 0.5 hour.

9. Collect the crystals by filtration. Tamp the filter cake to eliminate cracks and channels.

10. Wash the filter cake with 20 ml. sterile, pyrogen-free 90% acetone - 10% deionized water (v/v) solution and then with 50–60 ml. sterile, pyrogen-free acetone.

11. Vacuum-dry the sterile crystalline sodium BL-S786 at 50°–56° C. for 24 hours under sterile conditions. Expected yield: 7.5–9.0 gm. (bio-yield=70–92%).

| Properties of Crystalline Sodium BL-S786 Dihydrate | |
|---|---|
| Bio-potency | = 950–1,000 units/mg. |
| % ash as sodium | = 3.71 (theory for monosodium salt = 3.91%) |
| % water (KF) | = 6.0 (theory for dihydrate = 6.22) |
| NMR | = Excellent spectrum. No evidence of any specific impurities. |
| Solubility in water | = >400 mg./ml. |
| pH of a 300 mgm./ml. solution | = 4.8–7.3 |
| Stability of 250,000 unit/ml. solution | = No loss for 24 hours at room temperature. |
| Klett Color (Blue Filter No. 42): | 1% in water = 30–35  10% in water = 400–450 |

EXAMPLE 9

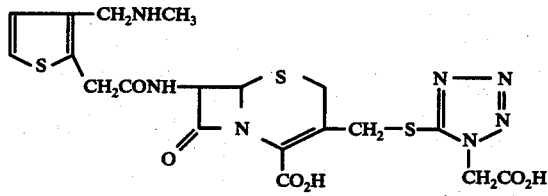

BB-S444

7-(3-N-t-butoxycarbonyl-N-methylaminomethyl-2-thienylacetamido)-3-(1-carboxymethyltetrazol-5-ylthiomethyl)-3-cephem-4-carboxylic Acid A mixture of 3-(N-t-butoxycarbonyl-N-methylaminomethyl)-2-thienylacetic acid (855 mg., 3 m.moles), 2,4-dinitrophenol (552 mg., 3 m.moles) and DCC (618 mg., 3 m.moles) in THF (10 ml.) was stirred at room temperature for 1.5 hours. The precipitated urea was removed and the filtrate was added to a mixture of 7-amino-3-(1-carboxymethyltetrazol-5-ylthiomethyl)-3-cephem-4-carboxylic acid (1.1 g., 3 m.moles) and triethylamine (909 mg., 9 m.moles) in water (10 ml.) with stirring at 0° C. Stirring was continued for 3.5 hours at room temperature and the reaction mixture was added to water (20 ml.) and washed with ether (20 ml.). The aqueous solution was layered with ethyl acetate (20 ml.) and adjusted to pH 2 with concentrated HCl at 5° C. The organic layer was separated and the aqueous layer was extracted with ethyl acetate (3 × 50 ml.). The ethyl acetate extracts were combined, washed with a saturated aqueous NaCl solution, dried over MgSO$_4$, and concentrated under reduced pressure. The residual oil (1.1 g.) was chromatographed on a silica gel column (11 g.). The column was eluted successively with chloroform (400 ml.) and 3% methanol-chloroform (400 ml.). From the chloroform eluate 2,4-dinitrophenol (150 mg.) was recovered. The 3% methanol-chloroform eluate was cut into two fractions on the basis of TLC on silica gel plate (50% MeOHCHCl$_3$, detected with I$_2$). The first fraction was a mixture (100 mg.) of BOC-protected amino acid and the product. The second fraction contained 610 mg., 32% Rf: 0.24), m.p. 175°–180° C. (dec.), of the title compound.

ir: $\eta_{max}^{KBr}$ 3220, 1780, 1740, 1660 cm$^{-1}$.

nmr: $\delta_{ppm}^{DMSO-d6}$ 1.41 (9H, s, BOC-H), 2.71 (3H, s, NCH$_3$BOC), 3.70 (2H, br-s, 2-H), 3.79 (2H, s, CH$_2$CO), 4.32 (4H, s, 3-CH$_2$ & N-CH$_2$), 5.05 (1H, d, J=4.5 Hz, 6-H), 5.27 (2H, s, N-CH$_2$CO$_2$H), 5.67 (1H, d-d, J=4.5 & 9Hz, changed to a doublet, J=4.5 Hz, by addition of D$_2$O, 7-H) 6.84 (1H, d, J=6 Hz, thiophene-H$\beta$), 7.35 (1H, d, J=6 Hz, thiopheneH$\alpha$), 9.16 (1H, d, J=9 Hz, disappeared by addition of D$_2$O, CONH).

Anal. Calc'd. for C$_{24}$H$_{29}$N$_7$O$_8$S$_3$.$\frac{3}{4}$H$_2$O: C, 44.23; H, 4.69; N, 15.04; S, 14.76. Found: C, 44.79; H, 4.63; N, 14.49; S, 14.15.

BB-S444;
7-(3-N-methylaminomethyl-2-thienylacetamido)-3-(1-carboxymethyltetrazol-5-ylthiomethyl)-3-cephem-4-carboxylic Acid Trifluoroacetic acid (0.5 ml.) was added to 7-(3-N-t-butoxycarbonyl-N-methylaminomethyl-2-thienylacetamido)-3-(1-carboxymethyltetrazol-5-ylthiomethyl)-3-cephem-4-carboxylic acid (539 mg., 0.84 m.moles) at 0° C. and the mixture was stirred at room temperature for 15 minutes. To the reaction mixture was added anhydrous ether (10 ml.) to separate precipitate, which was collected by filtration, washed with anhydrous either (2 × 10 ml.) and suspended in acetonitrile (10 ml.). To the suspension was added 2 drops of concentrated ammonium hydroxide. The separated solid was collected by filtration, washed with acetonitrile (2 × 10 ml.) and dried at 60° C./1 mmHg for 7 hours to afford 327 mg. (72%) of 7-(3-N-Methylaminomethyl-2-thienylacetamido)-3-(1-carboxymethyltetrazol-5-ylthiomethyl)-3-cephem-4-carboxylic acid, melting at 171°–175° C. (dec.) and identified as BB-S444.

ir: $\eta_{max}^{KBr}$ 3200, 1770, 1670, 1610 cm$^{-1}$.

uv: $\lambda_{max}^{Buffer(pH7)}$ 237 nm ($\epsilon$, 16200), 265 nm ($\epsilon$, 10300)

Anal. Calc'd. for C$_{19}$H$_{21}$N$_7$O$_6$S$_3$. 3/2H$_2$O: C, 40.27; H, 4.27; N, 17.30; S, 16.98. Found: C, 39.99; H, 4.14; N, 17.39; S, 16.12.

Sodium salt of BB-S444

To a suspension of BB-S444 (87 mg., 0.16 m.moles) in water (10 ml.) was added 2.6 ml. of 47.5 × 10$^{-3}$ M NaOH solution to adjust to pH 7.2 and the mixture was treated with charcoal and lyophilized to afford 87 mg. of light brown powder melting at 167°–171° C.

ir: $\eta_{max}^{KBr}$ 3200, 1770, 1640, 1600 cm$^{-1}$.

uv: $\lambda_{max}^{Buffer(pH7)}$ 237 nm ($\epsilon$, 15900), 265 nm ($\epsilon$, 10000).

Anal. Calc'd. for C$_{19}$H$_{29}$N$_7$O$_6$S$_3$Na.3H$_2$O: C, 37.07; H, 4.26; N, 15.93; S, 15.93; S, 15.62. Found: C, 37.27; H, 4.22; N, 16.33; S, 14.95.

| MIC (mcg./ml.) by Tube Dilution Technique in Nutrient Broth. | | | |
|---|---|---|---|
| Organism | Compound of Example 9 (BB-S444) | Compound of Example 1 (BL-S786) | Cefamandole |
| Dp-4 D. pneumoniae A9585 | 0.08 | 0.16 | 0.08 |
| Sp-3 S. pyogenes A9604 | 0.08 | 0.16 | 0.08 |
| Sa-2 S. aureus Smith A9537 | 3.1 | 3.1 | 0.8 |
| Sa-2 S. aureus +50% serum | 3.1 | >3.1 | 1.6 |
| Sa-11 S. aureus BX-1633 A9606 | 6.3 | 3.1 | 1.6 |
| Sa-44 S. aureus A15097 | 12.5 | 6.3 | 3.1 |
| Se-1 S. enteritidis A9531 | 0.2 | 0.2 | 0.4 |
| Ec-1 E. coli NIHJ | 0.8 | 0.8 | 1.6 |

| MIC (mcg./ml.) by Tube Dilution Technique in Nutrient Broth. | | | |
|---|---|---|---|
| Organism | Compound of Example 9 (BB-S444) | Compound of Example 1 (BL-S786) | Cefamandole |
| Ec-3 E. coli Juhl A15119 | 0.8 | 0.8 | 0.8 |
| Ec-58 E. coli A9675 | 12.5 | 6.3 | 3.1 |
| Kp-3 K. pneumoniae A9977 | 0.2 | 0.2 | 0.8 |
| Kp-4 K. pneumoniae A15130 | 1.6 | 1.6 | 6.3 |
| Pm-2 P. mirabilis A9900 | 0.4 | 0.4 | 0.8 |
| Pg-8 P. morganii A15153 | 12.5 | 6.3 | 3.1 |
| Pg-8 P. aeruginosa A9843 | >100 | >100 | >100 |
| Sm-1 S. marcescens A20019 | >100 | >100 | >100 |
| El-1 E. cloacae A9656 | 50 | 50 | 50 |

EXAMPLE 10

7-(2-Aminomethylphenylacetamido)-3-(1-carboxypropyltetrazol-5-ylthiomethyl)-3-cephem-4-carboxylic Acid. (BL-S1046)

A mixture of 1.57 g. (0.0052 mole) of potassium 2-N-(1-carbethoxypropen-2-yl)aminomethylphenyl acetate and 5 drops of N,N-dimethylbenzylamine in 50 ml. of tetrahdrofuran at −40° C. was stirred vigorously with 720 mg. (0.0053 mole) of isobutyl chloroformate. The mixture was stirred for an additional 25 minutes and added to a solution of 1.38 g. (.0034 mole) of 7-amino-3-(1-carboxypropyltetrazol-5-thiomethyl)-3-cephem-4-carboxylic acid and 0.975 ml. (0.0089 mole) of N-methyl-morpholine in 28 ml. of water at 5° C. The solution was stirred for 1 hour and the tetrahydrofuran was removed at 30° C. (15 mm.) and layered with 50 ml. of ethyl acetate. The mixture was adjusted to pH 4.5 with concentrated hydrochloric acid and filtered to remove some dark brown material. The filtrate was adjusted dropwise to pH 3.5 with concentrated hydrochloric acid and the product was collected, washed with cold water and with cold methanol to yield after drying in vacuo for 64 hours over phosphorous pentoxide 420 mg. 7-(2-aminomethylphenylacetamido)-3-(1-carboxypropyltetrazol-5-ylthiomethyl)-3-cephem-4-carboxylic acid, m.p. 130° (slow decomp.).

Anal. Calc'd. for $C_{22}H_{25}N_7O_6S_2 \cdot H_2O$: C, 46.71; H, 4.80; N, 17.34. Found: C, 46.55; H, 4.94; N, 16.25. The ir and nmr spectra were consistent for the structure.

Laboratory Evaluation of BL-S786, 7-[α-(2-aminomethylphenyl)acetamido]-3-[(1-carboxymethyltetrazol-5-ylthio)methyl]-3-cephem-4-carboxylic Acid.

Bacteria. The organisms, preponderantly of recent clinical origin, were obtained from numerous sources of broad geographical distribution. Obligate anaerobes were maintained in Egg Meat Medium (Difco); Mycobacterium was stored on Lowenstein Medium [Jensen Modification; Difco). The techniques of storing all other organisms have been described previously (Leitner et al., BL-S640, A Cephalosporin with a Broad Spectrum of Antibacterial Activity: Properties in vitro, Antimicrob. Agents Chemother. 7:298–305 (1975)].

Antibiotic spectrum. The growth-inhibitory activity of BL-S786 and the control compounds was determined by the antibiotic dilution technique. Procedures were as follows:

a. Aerobic organisms (excluding Mycobacterium). Except for Haemophilus and Neisseria, the assay was performed in Mueller-Hinton Medium (Difco). For fastidious organisms, i.e., Streptococcus, Listeria, Pasteurella, Bordetella and Vibrio, the medium was supplemented with 4% defibrinated sheep blood. The antibiotic susceptibility of Haemophilus and Neisseria was determined in GC Medium Base (BBL) supplemented with 1% Hemoglobin (BBL) and 1% Isovitalex (BBL).

Overnight broth cultures of an exponentially growing culture (Neisseria) served as the source of inoculum. A volume of approximately 0.003 ml. of the undiluted or diluted culture was applied to the surface of the antibiotic-containing agar plates with the inoculator of Steers et al., An Inocula Replicating Apparatus for Routine Testing of Bacterial Susceptibility to Antibiotics, Antibiot. Chemother. 9:307–311 (1959). Cultures of Neisseria, Streptococcus pneumoniae, S. viridans and S. pyogenes were used without dilution; those of all other organisms were diluted 100-fold. The inoculum contained about $10^3$ viable cells for Neisseria, $10^5$ for S. pneumoniae and S. pyogenes, $10^6$ for S. viridans, and $10^4$ for all other species. The culture plates were incubated at 37° C. either overnight or for 24 hours (Haemophilus) and the minimum inhibitory concentration (MIC), i.e., the lowest concentration of antibiotic which prevents visible growth, was recorded.

b. Mycobacterium tuberculosis. Antimycobacterial activity was assayed in Dubos Liquid Medium (Difco). To 1 ml. of anitbiotic-containing medium, 3 ml. of a 50-fold diluted 10-day old culture were added. MIC values were determined after further incubation at 37° C. for 10 days.

c. Obligate anaerobes. The assay was performed on solid medium, consisting of Brain Heart Infusion Broth (BBL) supplemented with 5% defibrinated sheep blood and 1% Ionagar (Colab). A volume of approximately 0.003 ml. of a cell suspension, containing $10^4$ viable cells, was applied to the surface of the medicated agar plates with the inoculator of Steers et al. (ibid.). The plates were incubated at 37° C. for 48 hours under the oxygen-free conditions attained with a Gas-Pak (BBL) Brewer jar system.

Binding to Serum Proteins. The degree of binding of human serum proteins was estimated by means of the antibiotic diffusion technique of Scholtan and Schmid, Die Bindung der Penicilline an die Eiweisskorper des Serums und des Gewebes, Arzneim. Forsch. 12:741–750 (1962). The assays were performed in 95% pooled human serum. The range of cephalosporin concentrations was as follows: 3 to 20 mcg./ml. for BL-S786; 1 to 20 mcg./ml. for cephalothin; 0.5 to 5 mcg./ml. for cephaloridine; and 4 to 100 mcg./ml. for cefazolin.

Stability in Solution. Stability in solution was determined at 37° C. in 0.005 M phosphate buffer of pH 7.4. The initial antibiotic concentration was 0.2 mg./ml. for cephalothin, 0.6 mg./ml. for BL-S786 and cefazolin and 2 mg./ml. for cephaloridine. Residual antibiotic activity was determined periodically over a 24-hour period by a turbidimetric assay procedure or by an antibiotic diffusion technique (cephalothin).

Antibiotic Concentration in Blood. Male Swiss-Webster mice, weighing 19–22 g., were given 0.2 ml. of antibiotic solutions at appropriate concentrations by intramuscular injection. The vehicle was 0.01% phosphate buffer at pH 7.0. Eight animals were used for each dose level (5, 10, 20 and 40 mg./kg.). Blood samples (0.03 ml.) were obtained from the orbital sinuses by means of heparinized capillary tubes (Clay Adams) at 0.25, 0.5, 1 and 1.5 hours after administration of the compound. Paper discs, 6.35 mm. in diameter, were impregnated with the blood and the antibiotic activity assayed by the diffusion technique using Seed Agar (BBL) inoculated with *Bacillus subtilis* ATCC 6633. A standard line relating the diameter of the inhibition zone to drug concentration was obtained by assaying the compounds at known concentrations in heparinized mouse blood.

Recovery in Urine. Male Sprague-Dawley rats, weighing 180–220 g., received a dose of 10 mg./kg. antibiotic in 0.4 ml. of 0.01% phosphate buffer at pH 7.0 by intramuscular injection. Depending on the experiment, 4, 5 or 10 rats were used per compound. The animals were hydrated with 5 ml. of water 0, 3 and 6 hours after dosing. The rats were housed individually in metabolism cages and urine specimens were collected over dry ice during intervals of 0–6 and 6–24 hours after administration. Aliquots (0.03 ml.) of appropriate dilutions of urine were placed on paper discs (6.35 mm. in diameter) and the antibiotic activity was assayed by the diffusion technique on Seed Agar inoculated with *B. subtilis* ATCC 6633. A standard line relating the diameter of the inhibition zone to drug concentration was obtained by assaying the compounds at known concentrations in urine collected from untreated control animals.

Treatment of Systemically Infected Mice. The procedures were identical with those published previously [Leitner et al., BL-S640, a Cephalosporin With a Broad Spectrum of Antibacterial Activity: Bioavailability and Therapeutic Properties in Rodents, Antimicrob. Agents Chemother. 7:306–310, (1975)], except that:

(a) the hog gastric mucin used in infections with *Staphylococcus aureus* No. 2 was purchased from American Laboratories, Inc., Omaha, Neb. (lot No. 154163) and b) that the medium used to suspend all other organisms contained 3% (rather than 4%) hog gastric mucin (type 1701W, Wilson Laboratories, Inc., Park Forest South, Ill.).

Miscellaneous. Methods for determining bactericidal activity and susceptibility to cell-free β-lactamase were those previously used; Leitner et al., BL-S640, A Cephalosporin With a Broad Spectrum of Antibacterial Activity: Properties in vitro, Antimicrob. Agents Chemother. 7:298–305 (1975).

RESULTS

Properties in Vitro. Antibiotic Spectrum. The growth inhibitory activity of BL-S786 and the three control cephalosporins is illustrated in Tables 1 and 2.

BL-S786 was from 2 to 16 times more active than the reference cephalosporins against *Escherichia coli*, *Klebsiella pneumoniae*, *Proteus mirabilis*, *Proteus vulgaris*, *Salmonella* sp., *Shigella* sp. and *Neisseria meningitidis*. BL-S786 was also the most active of the four cephalosporins against a small number of strains of *Edwardsiella tarda*, *Arizona hinshawii*, and *Erwinia* sp. (Table 1). Ninety-eight percent of the *Providencia stuartii* and 78% of the *Proteus rettgeri* strains were inhibited by BL-S786 at a concentration of 16 mcg./ml. At the same concentration, cefazolin inhibited 23% and 44% of the strains, respectively, whereas the percentage of strains inhibited by cephalothin and cephaloridine was negligible for both species. Against *Enterobacter* sp. and *Citrobacter* sp., BL-S786 alone was active. Against *Haemophilus influenzae*, including 9 ampicillin-resistant strains, BL-S786, cephaloridine, and cefazolin were about equally active, whereas cephalothin was more than twice as active as the other cephalosporins. *Neisseria gonorrhoeae* was equally susceptible to BL-S786, cephalothin and cefazolin. Five strains of *Alcaligenes* sp. were susceptible and six were resistant to the four cephalosporins. *Pasteurella multocida* was highly susceptible, whereas *Proteus morganii*, *Serratia marcescens*, *Pseudomonas aeruginosa* and *Bacteroides fragilis* were resistant to all of the cephalosporins.

BL-S786 was generally less active than the control compounds against staphylococci, streptococci, *Listeria monocytogenes* and *Clostridium* sp. (Table 2). Nevertheless, BL-S786 at 4 mcg./ml. inhibited 62 strains and at 8 mcg./ml. all 63 strains of *S. aureus*. Furthermore, BL-S786 inhibited all strains of *S. pneumoniae* at 0.25 mcg./ml. of *S. pyogenes* at 0.5 mcg./ml. and of *S. viridans* at 4 mcg./ml. The three strains of Clostridium sp. were inhibited at 2 mcg./ml. BL-S786 was 4 to 32 times more active than the control compounds against *M. tuberculosis* H37Rv. *Streptococcus faecalis* was resistant to BL-S786.

Effect of Inoculum Size. A variation in the initial cell concentration of Enterobacteriaceae affected in a similar fashion the growth inhibitory activity of BL-S786 and of the control compounds (Table 3). Thus, with few exceptions, the activity of all compounds declined sharply (from 16- to more than 1000-fold) against strains of *Enterobacter cloacae*, *E. aerogenes* and *P. rettgeri*, but only moderately (from 2- to 8-fold) against strains of *E. coli*, *K. pneumoniae*, *P. mirabilis* and *P. vulgaris* when the inoculum was increased from $10^2$ to $10^6$ organisms.

The effect of inoculum on the susceptibility of staphylococci to cephalosporins is illustrated in Table 4. The susceptibility of strains that lack penicillinase varied little with initial cell concentration. With penicillinase-producing strains, cell concentration affected only slightly the growth inhibitory activity of BL-S786 and cephalothin, moderately that of cefazolin and sharply that of cephaloridine.

Bactericidal Activity. BL-S786 and the control compounds were effective bactericidal agents for strains of E. coli, K. pneumoniae, P. mirabilis and *P. vulgaris* (Table 5). For most strains of Enterobacter, BL-S786 alone was significantly bactericidal. One strain of *P. rettgeri* was susceptible, the other largely resistant to the bactericidal action of the cephalosporins.

Susceptibility to β-lactamase. Susceptibility to enzymic hydrolysis was assessed by determining relative rates of hydrolysis by cell-free preparations of various β-lactamases (Table 6). BL-S786 was slightly to markedly less susceptible than the other cephalosporins to hydrolysis by β-lactamases of Type I$a$, I$b$, III$a$ and IV$a$. All cephalosporins were poor substrates for Type II$a$ and staphylococcal β-lactamases. The four cephalosporins were hydrolyzed at similar rates by the Type IV$b$ enzyme.

Binding to Serum Proteins. In 95% human serum, BL-S786 and cephalothin were 67%, cephaloridine was 30% and cefazolin 76% protein bound.

Stability in Solution. At pH 7.4 and 37° C. the half-life of BL-S786 and the control cephalosporins was greater than 24 hours.

Properties In Vitro. Concentration in Murine Blood. Peak antibiotic concentrations of BL-S786 and the three control compounds were observed 0.25 hour after intrasmuscular administration. At a dose of 20 mg./kg. BL-S786 reached a peak concentration of 36 mcg./ml. compared to 31 mcg./ml. for cefazolin, 23 mcg./ml. for cephaloridine and 17 mcg./ml. for cephalothin. The concentration of BL-S786 in the blood declined at a slower rate ($t_{1/2}$ of 33 min.) than that of the control cephalosporins ($t_{1/2}$ of 11 min. for cephalothin, 22 min.

for cephaloridine and 25 min. for cefazolin). With all compounds peak concentrations were essentially proportional to dose in the range tested.

Recovery in Rat Urine. Rats, receiving intramuscularly 10 mg. of BL-S786 per kg. body weight, excreted an average of 65% of the administered dose in urine. Comparable fractions of the dose were recovered when cephaloridine or cefazolin were given (59 and 75% of the dose, respectively). By contrast, only 22% of the cephalothin dose was accounted for in the urine. With all cephalosporins over 96% of the recoverable dose was excreted within 6 hours of administration.

Treatment of Systemically Infected Mice. Against infections with *E. coli* and *K. pneumoniae* (Table 7), BL-S786 given intramuscularly was either more active than the control cephalosporins (*E. coli* 1, *K. pneumoniae* 1) or at least as active as the most active of these compounds (*E. coli* 8 and 9, *K. pneumoniae* 7). In the treatment of infections with *P. mirabilis, P. vulgaris, P. morganii, P. rettgeri Citrobacter* sp. and *P. stuartii*, BL-S786 was more active than the control cephalosporins. Against infections with *Enterobacter cloacae*, BL-S786 alone was effective.

In the treatment of streptococcal infections, BL-S786 was generally more active than cehalothin but less active than cephaloridine and cefazolin (Table 8). Against staphylococcal infections, there was no well-defined efficacy pattern but BL-S786 was at least as active as cephalothin.

DISCUSSION

BL-S786 compared favorably with cephalothin, cephaloridine and cefazolin in activity and bioavailability. The compound had a broader spectrum of antibacterial activity then cephalosporins currently available for clinical use. Thus, it was active against the majority of strains of *Enterobacter* sp., *P. rettgeri, P. stuartii* and *Citrobacter* sp., organisms highly resistant to the other cephalosporins. With few exceptions (*H. influenzae, N. gonorrhoeae*), BL-S786 was more active in vitro against major gram-negative pathogenic species than any of the three control cephalosporins. This advantage of BL-S786 was borne out in vivo. Although BL-S786 was generally less active than the reference compounds against gram-positive pathogens, it inhibited their growth at concentrations that should readily be achieved in man after standard parenteral dosage. *S. faecalis*, a species relatively insensitive to cephalosporins in general, was an exception. BL-S786 was an effective bactericidal agent for strains of various gram-negative species including *E. cloacae* and *E. aerogenes*. When given intramuscularly to mice, BL-S786 achieved high concentrations in blood and its biological half-life was longer than that of the other three cephalosporins. Two-thirds of the dose administered intramuscularly to rats was recovered in urine.

TABLE 1.

| | | Minimum inhibitory concentration* (mcg./ml.) | | | |
|---|---|---|---|---|---|
| Organism | No. of Strains | BL-S786 | Cephalothin | Cephaloridine | Cefazolin |
| Edwardsiella tarda | 2 | 0.13 | 1 | 1 | 0.71 |
| Arizona hinshawii | 2 | 0.13 | 2.8 | 2 | 1 |
| Citrobacter sp. | 4 | 1 | 63 | >125 | 75 |
| Citrobacter sp. | 1 | 125 | >125 | >125 | >125 |
| Serratia marcescens | 15 | >125 | >125 | >125 | >125 |
| Erwinia sp. | 5 | 0.66 | 5.3 | 2 | 1.5 |
| Vibrio cholerae | 1 | 4 | 1 | 16 | 4 |
| Pasteurella multocida | 2 | 0.25 | 0.09 | 0.5 | 0.5 |
| Pseudomonas aeruginosa | 16 | >125 | >125 | >125 | >125 |
| Alcaligenes sp. | 5 | 2.6 | 1.3 | 6.1 | 4.6 |
| Alcaligenes sp. | 2 | 63 | >125 | >125 | >125 |
| Alcaligenes sp. | 4 | >125 | >105 | >125 | >105 |
| Bordetella bronchiseptica | 1 | 125 | 8 | 32 | 125 |
| Bacteroides Fragilis | 3 | 100 | 125 | 79 | 50 |

Growth Inhibitory Acitvity Against Strains of Miscellaneous Gram-negative Organisms

*Geometric mean when applicable.

TABLE 2.

| | | Minimum inhibitory concentration$^a$ (mcg./ml.) | | | |
|---|---|---|---|---|---|
| Organism | No. of Strains | BL-S786 | Cephalothin | Cephaloridine | Cefazolin |
| Listeria monocytogenes | 7 | 10.8 | 2 | 0.91 | 1.2 |
| Clostridium sp. | 3 | 2 | 0.5 | 0.63 | 0.4 |
| Mycobacterium tuberculosis$^b$ | 2 | 4 | 63 | 16 | 125 |
| Mycobacterium tuberculosis$^c$ | 1 | 16 | 250 | 63 | 250 |

Growth Inhibitory Activity Against Strains of Miscellaneous Gram-positive Organisms $^a$Geometric mean when applicable.
$^b$Strain H37Rv: parent and streptomycin-resistant mutant.
$^c$Strain H37Rv: isoniazid-resistant mutant.

TABLE 3.

| | | Minimum Inhibitory Concentration (mcg./ml.)* | | | | | | |
|---|---|---|---|---|---|---|---|---|
| | | BL-S786 | | Cephalothin | | Cephaloridine | | Cefazolin | |
| Organism | Strain | A | B | A | B | A | B | A | B |
| Escherichia coli | 1 | 0.5 | 2 | 8 | 32 | 2 | 8 | 1 | 4 |
| | 3 | 0.25 | 1 | 4 | 16 | 2 | 4 | 1 | 2 |
| | 4 | 0.5 | 2 | 4 | 32 | 2 | 4 | 1 | 2 |
| | 5 | 1 | 2 | 4 | 32 | 4 | 8 | 1 | 2 |
| | 6 | 0.5 | 2 | 8 | 16 | 2 | 8 | 1 | 2 |
| | 7 | 0.25 | 2 | 1 | 8 | 2 | 4 | 1 | 2 |
| | 2 | 4 | 32 | 16 | 32 | 4 | 16 | 2 | 16 |
| Klebsiella | 1 | 0.5 | 1 | 2 | 8 | 2 | 4 | 1 | 2 |

Effect of Inoculum Size on the Susceptibility of *Enterobacteriaceae* ir: $\eta_{max}^{KBr}$ 1770, 1660, 1610, 1380 cm$^{-1}$.

uv: $\lambda_{max}^{Buff.(pH7)}$ 270 nm ($\epsilon$, 10000).

Anal. Calc'd. for $C_{20}H_{21}N_7O_7S_2 \cdot \frac{1}{2}CH_3CN$: C, 45.36; H, 4.08; N, 18.89; S, 11.53. Found: C, 45.53; H, 4.64; N, 18.44; S, 10.59.

EXAMPLE 14

Substitution in the procedure of Example 7 for the o-aminomethyl-phenylacetic acid used therein of an equimolar weight of o-aminomethyl-4-hydroxyphenylacetic acid and of o-N-methyl-aminomethyl-4-hydroxyphenylacetic acid and o-N-methyl-aminomethyl-4-methoxyphenylacetic acid, respectively, produces the compounds having the structures

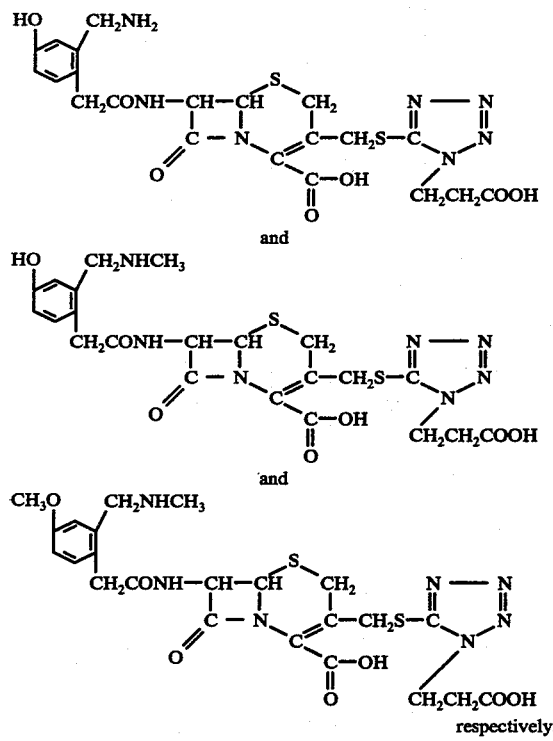

respectively.

EXAMPLE 15

7-α-(o-N-Methylaminomethylphenyl)acetamido-3-(1-carboxymethyltetrazol-5-ylthiomethyl)-3-cephem-4-carboxylic acid

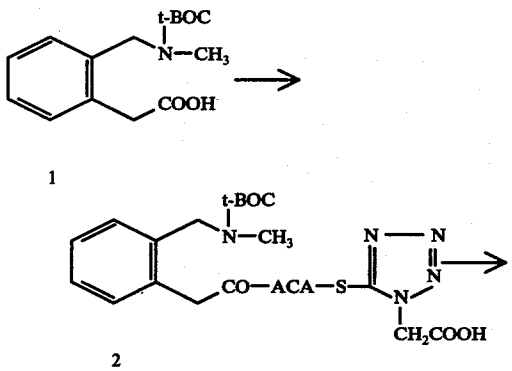

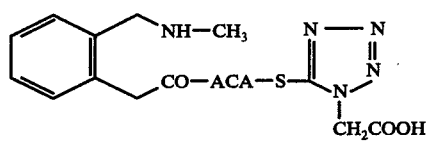

3. BB-S416

7-[α-o-(N-Methyl-N-t-Butoxycarbonylaminomethyl)-phenylacetamido]-3-(1-carboxymethyltetrazol-5-ylthiomethyl)-3-cephem-4-carboxylic acid (2)

A mixture of o-N-butoxycarbonyl-N-methylaminomethylphenylacetic acid (1) (558 mg., 2 mmol.), 2,4-dinitrophenol (368 mg., 2 mmol.) and DCC (412 mg., 2 mmol.) in THF (10 ml.) was stirred for 1 hour at room temperature. The precipitated urea was removed by filtration and washed with THF (5 ml.). The filtrate and washings were combined and added to a ice-cooled solution of 7-amino-3-(1-carboxymethyltetrazol-5-ylthiomethyl)-3-cephem-4-carboxylic acid (744 mg., 2 mmol.) and triethylamine (0.61 g., 6 mmol.) in 50% aqueous THF (20 ml.) with stirring and the stirring was continued overnight. The mixture was diluted with water (20 ml.) and washed with ether (3 × 50 ml.). The aqueous layer was acidified to pH 1 with dil. HCl and extracted with ethyl acetate (4 × 50 ml.). The combined extracts were washed with water, treated with a small amount of carbon and dried. Removal of the solvent under reduced pressure afforded an oily residue, which solidified by trituration with ether-n-hexane (1:1; 50 ml.). The product 2 was collected by filtration, washed with ether-n-hexane (1:1; 20 ml.) and dried. Yield 0.58 g. (46%). m.p. 120°–130° C. (dec.).

ir: $\eta_{max}^{KBr}$ 3600–2400, 1780, 1730, 1660, 1400, 1250, 1150 cm$^{-1}$.

nmr: $\delta_{ppm}^{DMSO-d_6}$ 1.45 (9H, s, t-Bu-H), 2.76 (3H, s, N-CH$_3$), 3.5–3.6 (4H, m, 2-H, CH$_2$CO), 4.2–4.6 (4H, m, 3-H and CH$_2$N), 5.05 (1H, d, 4Hz, 6-H), 5.40 (2H, s, N-C$\underline{H}_2$COOH), 5.66 (1H, d-d, 4 and 8Hz, 7-H), 7.21 (4H, s, phenyl-H), 9.10 (1H, d, 8Hz, CONH).

Anal. Calc'd. for $C_{26}H_{31}N_7O_8S_2$: C, 49.28; H, 4.93; N, 15.47; S, 10.12. Found: C, 50.57, 50.66; H, 4.89, 5.10; N, 13.88, 13.94; S, 9.58, 9.45.

7-α-(o-N-methylaminomethylphenyl)acetamido-3-(1-carboxymethyltetrazol-5-ylthiomethyl)-3-cephem-4-carboxylic acid (3)

The N-BOC cephalosporin 2 (0.54 g., 0.85 mmol.) was mixed with ice-cooled TFA (1.5 ml.) and the mixture was stirred for 10 minutes at room temperature. Ether (20 ml.) was added to the mixture to precipitate the TFA salt of 3 which was collected by filtration and dissolved in acetonitrile (50 ml.). The solution was treated with a small amount of carbon. To the filtrate was added dropwise conc. NH$_4$OH with stirring until no more precipitate was formed. The product 3 was collected by filtration, washed with acetonitrile (20 ml.) and dried. Yield 0.34 g. (75%). m.p. 177°–182° C. (dec.).

ir: $\eta_{max}^{KBr}$ 3600–2600, 1775, 1660(sh), 1620, 1385, 1205, 1180 cm$^{-1}$.

uv: $\lambda_{max}^{water}$ 267 nm ($\epsilon$, 9200).

nmr: $\delta_{ppm}^{D_2O+NaHCO_3}$ 2.80 (3H, s, N-CH$_3$), 3.4–3.6 (2H, m, 2-H), 3.84 (2H, s, CH$_2$CON), 4.1–4.3 (2H, m, 3-H), 4.28 (2H, s, CH$_2$N), 4.93 (1H, d, 4Hz, 6-H), 4.98 (2H, s, NC$\underline{H}_2$COOH), 5.56 (1H, d, 4Hz, 7-H), 7.48 (4H, s, phenyl-H).

Anal. Calc'd. for $C_{21}H_{23}N_7O_6S_2.2.5H_2O$: C, 43.59; H, 4.88; N, 16.94; S, 11.08. Found: C, 44.06, 43.96; H, 4.27, 4.55; N, 16.20, 16.50; S, 10.26, 10.30.

EXAMPLE 16

7-α-(o-N-Methylaminomethylphenyl)acetamido-3-(1-carboxyethyltetrazol-5-ylthiomethyl)-3-cephem-4-carboxylic acid Substitution in the procedure of Example 15 for the 7-amino-3-(1-carboxymethyltetrazol-5-ylthiomethyl)-3-cephem-4-carboxylic acid used therein of an equimolar weight of 7-amino-3-(1-carboxyethyltetrazol-5-ylthiomethyl)-3-cephem-4-carboxylic acid produces the title compound.

EXAMPLE 17

7-α-(o-N-Methylaminomethylphenyl)acetamido-3-(1-carboxypropyltetrazol-5-ylthiomethyl)-3-cephem-4-carboxylic acid Substitution in the procedure of Example 15 for the 7-amino-3-(1-carboxymethyltetrazol-5-ylthiomethyl)-3-cephem-4-carboxylic acid used therein of an equimolar weight of 7-amino-3-(1-carboxypropyltetrazol-5-ylthiomethyl)-3-cephem-4-carboxylic acid produces the title compound.

PREFERRED FORMULATIONS

The compounds of the present invention are preferably formulated for parenteral use as either their L-lysine, arginine or histidine salts or in physical admixture with L-lysine, arginine or histidine. This is exemplified below by detailed descriptions of the mixture and a salt of L-lysine and BL-S786 free acid prepared as a solid to be reconstituted by the addition of sterile water to give a solution suitable for parenteral injection which is fully active and stable within 10% at room temperature (23° C.) for eight hours at 250 mgm./ml. on an activity basis and for 24 hours at either 10 or 25 mgm./ml. of activity. The dry mixtures and salts are much more stable at elevated temperatures than either the crystalline or the amorphous sodium salts of BL-S786.

PARENTERAL GRADE L-LYSINE

Procedure (1.) Slurry 10 grams of L-Lysine in 75-100 ml. of methanol for 15 minutes at room temperature (22°-24° C.).

(2.) Remove the insolubles (mostly L-lysine carbonate or carbamate) by suitable filtration technique. Filtration is very slow and the solids are slimey. Discard the solids.

(3.) Add 1.5 grams of decolorizing charcoal ("Darco G-60") to the filtrate of step 2 and slurry for 0.5 hours.

(4.) Remove the carbon by filtration. Wash with 15 ml. of methanol. Add the wash to the filtrate.

(5.) Pass the filtrate wash through suitable filters to remove particles and bacteria.

(6.) In a sterile environment and using sterile techniques, add the sterile filtrate to 1 liter of rapidly stirring, sterile, pyrogen-free ethyl acetate. A precipitate forms. Slurry for 10 minutes.

(7.) Collect the precipitate by sterile filtration technique, wash with 75-100 ml. of sterile, pyrogen-free ethyl acetate and vacuum-dry at 60°-70° C. for 24 hours. Yield: Approximately 7 grams of L-Lysine. (Note: Sterile, pyrogen-free isopropanol may be substituted for the ethyl acetate, however, the resultant precipitate is very difficult to filter).

Preparation of Sterile, Parenteral Grade BL-S786 Free-Acid

Procedure I (1.) Ten grams of high purity (1000 mcg./mg., 25 Klett color) BL-S786 free-acid is slurried in 80 ml. of deionized water at 22°-25° C.

(2.) Ten percent sodium hydroxide is added with rapid stirring to pH 6.7-7.3. Stir at pH 6.8-7.3 for 5 minutes. A solution or near solution is obtained.

(3.) Add 1 gram of decolorizing charcoal ("Darco-KB") and slurry for 0.5 hour. Remove the carbon by filtration and wash with 10 ml. of water. Add the wash to the filtrate.

(4.) Pass the filtrate through suitable filters to remove particles and bacteria.

(5.) Using sterile technique, add sterile, pyrogen-free hydrochloric acid with rapid stirring to pH 1-1.4. Crystals form. Stir the mixture rapidly for 10 minutes.

(6.) Collect the crystals by filtration. Tamp the filter cake to remove cracks if present. Wash with 15-20 ml. of sterile, pyrogen-free water, 25 ml. of sterile, pyrogen-free acetone and vacuum-dry at sterile conditions at 56° C. for 24-48 hours. Yield: 9 grams + (%yield = >90) of BL-S786 free acid.

(7.) Under sterile conditions, pulverize to 200 mesh.

PROCEDURE II (1.) Slurry 10 grams of high purity (1000 mcg./mg., 25 Klett Color) BL-S786 free acid in 90 ml. of methanol at 22°-25° C.

(2.) Add concentrated hydrochloric acid with rapid stirring to an apparent pH of 0.7-1.0. A solution or near solution is obtained.

(3.) Add 1 gram of decolorizing charcoal ("Darco-KB") and slurry for 0.5 hour. Remove the carbon by filtration and wash with 15 ml. of methanol. Add the wash to the filtrate.

(4.) Pass the filtrate through suitable filters to remove particles and bacteria.

(5.) Using sterile technique, add sterile, pyrogen-free triethylamine with rapid stirring to an apparent pH of 2.7-3.5. Crystals form.

(6.) Remove the crystals by filtration. Wash with two 20 ml. portions of sterile, pyrogen-free methanol and with 20 ml. of sterile, pyrogen-free acetone.

(7.) Vacuum-dry at 56° C. for 24-48 hours. Yield 9 grams + (90%+).

(8.) Under sterile conditions, pulverize to 200 mesh.

PROPERTIES OF PARENTERAL GRADE BL-S786 FREE ACID (1.) Bio-assay: 1000-1050 mcg./mg.
(2.) % Water, KF = 1-3%
(3.) IR-NMR: Consistent for Structure
(4.) Klett Color (1% in 1% pH 7.0 phosphate buffer, using a #42 blue filter): 20-30

These two compounds are mixed in the following proportions:

| | |
|---|---|
| BL-S786 free-acid (1044 mcg./mg.) | = 0.480 gram |
| L-Lysine | = 0.168 gram |
| | 0.648 gram/vial |

EXAMPLE 11

7-[(2-N-Methylaminomethyl-4-methoxyphenyl-)acetamido]-3-(1-carboxymethyltetrazol-5-ylthiomethyl)-3-cephem-4-carboxylic acid

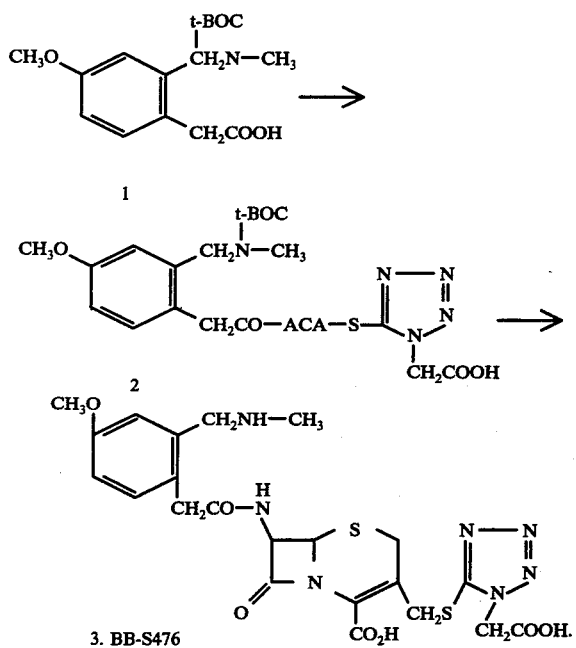

7-[(2-N-t-Butoxycarbonyl-N-methylaminomethyl-4-methoxyphenyl)-acetamido]-3-(1-carboxymethyltetrazol-5-ylthiomethyl)-3-cephem-4-carboxylic acid (2)

A mixture of 2-(N-t-butoxycarbonyl-N-methylaminomethyl)-4-methoxyphenyl-acetic acid (1) (680 mg., 2.2 mmol.), 2,4-dinitrophenol (405 mg., 2.2 mmol.) and DCC (453 mg., 2.2 mmol.) in dry THF (20 ml.) was stirred for 2 hours at room temperature. The urea which was separated was removed by filtration. The filtrate was added to an ice-cooled solution of 7-amino-3-(1-carboxymethyltetrazol-5-ylthiomethyl)-3-cephem-4-carboxylic acid (744 mg., 2 mmol.) and triethylamine (0.84 ml., 6 mmol.) in water (10 ml.) and the mixture was stirred for 3 hours at room temperature. The reaction mixture was concentrated to 10 ml. under reduced pressure, washed with ether (3 × 10 ml.), acidified with 6 N hydrochloric acid and extracted with ethyl acetate (5 × 10 ml.). The combined extracts were washed with a saturated saline water and dried with anhydrous $Na_2SO_4$. Evaporation of the solvent gave an oily product, which was chromatographed on a silica gel column (Wako-gel, C-100, 25 g.) by eluting with chloroform-methanol (0–3%). The fractions containing the desired product were collected, concentrated and triturated with ether-n-hexane to give the N-BOC cephalosporin 2 as an amorphous solid. Yield, 560 mg. (42%). m.p. 160°–170° C. (decomp).

ir: $\eta_{max}^{KBr}$ 1780, 1730, 1660, 1400 $cm^{-1}$.

uv: $\lambda_{max}^{Buff(pH7)}$ 225 nm ($\epsilon$, 15000), 270 ($\epsilon$, 10000).

nmr: $\delta_{ppm}^{DMSO-d_6}$ 1.09 (3H, t, $CH_3$ of ether), 1.39 (9H, s, BOC-H), 2.72 (3H, s, N-$CH_3$), 3.68 (3H, s, $OCH_3$), 4.99 (1H, d, 4.5 Hz, 6-H), 5.23 (2H, s, N-$CH_2COOH$), 5.58 (1H, d-d, 8 & 4.5 Hz, 7-H).

Anal. Calc'd. for $C_{27}H_{33}N_7O_9S_2 \cdot \frac{1}{2}(C_2H_5)_2O$: C, 49.70; H, 5.46; N, 13.99; S, 9.15. Found: C, 50.17; H, 5.77; N, 13.47; S, 8.79.

7-[(2-N-Methylaminomethyl-4-methoxyphenyl-)acetamido]-3-(1-carboxymethyltetrazol-5-ylthiomethyl)-3-cephem-4-carboxylic acid (3)

A mixture of the N-BOC cephalosporin 2 (500 mg., 0.75 mmol.) and TFA (1 ml.) was stirred for 15 min. at 10° C. Ether (50 ml.) was added to the mixture to precipitate the TFA salt of 3, which was collected by filtration and dissolved in a mixture of acetonitrile (20 ml.) and water (5 ml.). The solution was treated with active carbon. The filtrate was adjusted at pH 6 with conc. $NH_4OH$ and diluted with acetonitrile (100 ml.). The separated solid was collected by filtration, washed with acetonitrile (2 × 5 ml.) and dried in vacuo on $P_2O_5$ to afford 330 mg. (79%) of 3. m.p. 180°–190° C. (decomp).

ir: $\eta_{max}^{KBr}$ 1770, 1660, 1610, 1390 $cm^{-1}$.

uv: $\lambda_{max}^{Buffer(pH7)}$ 227 nm ($\epsilon$, 16000), 270 nm ($\epsilon$, 10000).

nmr: $\delta_{ppm}^{D_2O+NaHCO_3}$ 2.77 (3H, s, N-$CH_3$), 3.4–3.6 (2H, unresolved, 2-H), 3.6–3.95 (5H, unresolved, $OCH_3$ & $CH_2N$ & $CH_2CO$), 4.1–4.3 (4H, unresolved, $CH_2N$ & 3-$CH_2$), 4.95 (2H, s, N-$CH_2COOH$), 4.9 (1H, d, 0.45 Hz, 6-H), 5.53 (1H, d, 4.5 Hz, 7-H), 6.8–7.5 (3H, m, phenyl-H).

Anal. Calc'd. for $C_{22}H_{25}N_7O_7S_2 \cdot \frac{1}{2}H_2O$: C, 46.15; H, 4.58; N, 17.12; S, 11.20. Found: C, 45.89; H, 4.93; N, 17.27; S, 10.45.

EXAMPLE 12

7-[(2-N-Methylaminomethyl-4-hydroxyphenyl-)acetamido]-3-(1-carboxymethyltetrazol-5-ylthiomethyl)-3-cephem-4-carboxylic acid

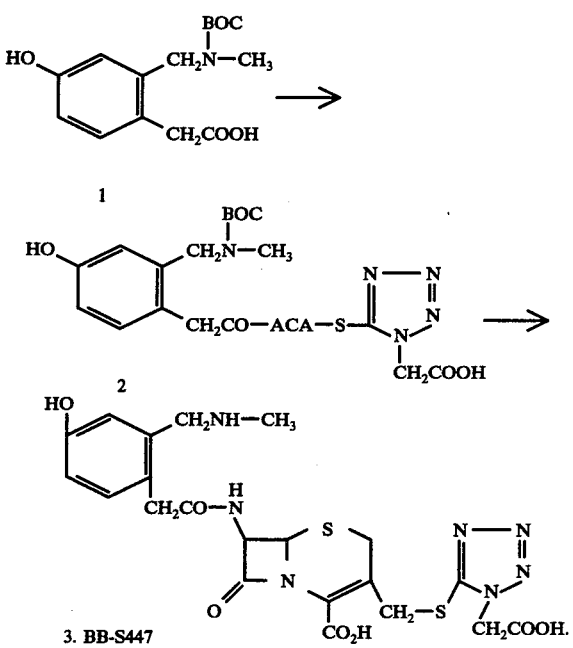

7-[(2-N-t-Butoxycarbonyl-N-methylaminomethyl-4-hydroxyphenyl)-acetamido]-3-(1-carboxymethyltetrazol-5-ylthiomethyl-3-cephem-4-carboxylic acid (2)

To a mixture of 2-N-t-butoxycarbonyl-N-methylaminomethyl-4-hydroxyphenyl-acetic acid (708 mg., 2.4 mmol.) and 2,4-dinitrophenol (478 mg., 2.6 mmol.) in dry THF (30 ml.) was added DCC (536 mg., 2.6 mmol.) in one portion and the mixture was stirred for 2 hours at room temperature. The precipitate was removed by filtration and the filtrate was added to a solution of 7-amino-3-(1-carboxymethyltetrazol-5-ylthiomethyl)-3-cephem-4-carboxylic acid (744 mg., 2 mmol.) and triethylamine (0.84 ml., 6 mmol.) in water (20 ml.). The mixture was stirred for 17 hours at room temperature. The reaction mixture was concentrated under diminished pressure to 20 ml., washed with ether (3 × 10 ml.), acidified with 6 N hydrochloric acid and extracted with ethyl acetate (3 × 20 ml.). The combined extracts were washed with saturated saline water and dried with anhydrous $Na_2SO_4$. Evaporation of the solvent under reduced pressure afforded an oily product, which was chromatographed on silica gel (Wako-gel, C-200, 25 g.) by eluting with chloroform-methanol (0-3%). The fractions which contained the desired product were collected and the solvent was removed in vacuo. The residual oil was triturated with ether-n-hexane to afford 474 mg. (36.5%) of amorphous, solid 2. m.p. 170°–180° C. (decomp.).

ir: $\eta_{max}^{KBr}$ 1780, 1660, 1400, 1250, 1150 cm$^{-1}$.

uv: $\lambda_{max}^{Buff.(pH7)}$ 270 nm ($\epsilon$, 7500).

nmr: $\delta_{ppm}^{DMSO-d_6}$ 1.39 (9H, s, BOC-H), 2.71 (3H, s, N-CH$_3$), 4.97 (1H, d, 4.5 Hz, 6-H), 5.21 (2H, s, N-CH$_2$COOH).

Anal. Calc'd. for $C_{26}H_{31}N_7O_9S_2.(C_2H_5)_2O$: C, 49.78; H, 5.71; N, 13.55; S, 8.86. Found: C, 49.78; H, 5.37; N, 13.44; S, 8.11.

7-[(2-N-Methylaminomethyl-4-hydroxyphenyl)acetamido]-3-(1-carboxymethyltetrazol-5-ylthiomethyl)-3-cephem-4-carboxylic acid (3)

The N-BOC protected cephalosporin 2 (400 mg., 0.62 mmol.) was treated with cold TFA (1 ml.) for 30 min. The TFA salt of 3 isolated by the addition of ether (50 ml.) was dissolved in acetonitrile (10 ml.)-water (5 ml.). After treating with a small amount of active carbon, the filtrate was adjusted to pH 6 with conc. ammonium hydroxide. The deposited precipitate of 3 was collected, washed with acetonitrile (10 ml.) and dried. Yield 200 mg. (59%). m.p. 190°–200° C. (decomp.).

ir: $\eta_{max}^{KBr}$ 1770, 1660, 1610, 1380 cm$^{-1}$.

uv: $\lambda_{max}^{Buff.(pH7)}$ 225 nm ($\epsilon$, 14000), 270 nm ($\epsilon$, 9700).

nmr: $\delta_{ppm}^{D_2O+K_2CO_3}$ 2.37 (3H, s, N-CH$_3$), 3.3–3.75 (4H, m, 2-H, CH$_2$CO), 3.9–4.4 (4H, m, CH$_2$N & 3-CH$_2$), 4.93 (2H, s, N-CH$_2$COOH), 4.85 (1H, d, 4.5 Hz, 6-H), 5.49 (1H, d, 4.5 Hz, 7-H), 6.6–7.3 (3H, m, phenyl-H).

Anal. Calc'd. for $C_{21}H_{23}N_7O_7S_2.H_2O$: C, 44.44; H, 4.44; N, 17.27; S, 11.30. Found: C, 44.82; H, 4.59; N, 16.90; S, 10.24.

EXAMPLE 13
7-[(2-Aminomethyl-4-hydroxyphenyl)acetamido]-3-(1-carboxymethyltetrazol-5-ylthiomethyl)-3-cephem-4-carboxylic acid

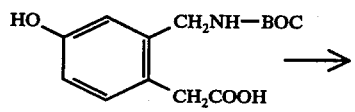

1

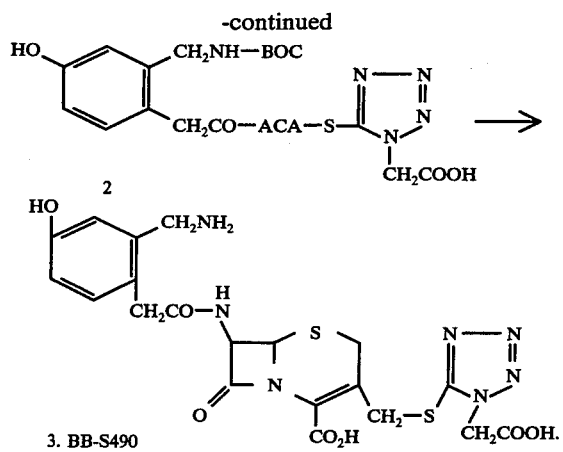

3. BB-S490

7-[(2-N-t-Butoxycarbonylaminomethyl-4-hydroxyphenyl)acetamido]-3-(1-carboxymethyltetrazol-5-ylthiomethyl)-3-cephem-4-carboxylic-acid (2)

Dicyclohexylcarbodiimide (513 mg., 2.5 mmol.) was added to a mixture of 2-N-t-butoxycarbonylaminomethyl-4-hydroxyphenylacetic acid (1) and 2,4-dinitrophenol (460 mg., 2.5 mmol.) in dry THF (20 ml.) and the mixture was stirred for 1 hour at room temperature. The urea which deposited was removed by filtration and the filtrate was added to a mixture of 7-amino-3-(1-carboxymethyltetrazol-5-ylthiomethyl)-3-cephem-4-carboxylic acid (744 mg., 2 mmol.) and triethylamine (0.56 ml., 4 mmol.) in 10 ml. of water. The mixture was stirred for 16 hours at room temperature and concentrated to 10 ml. under diminished pressure. The concentrate was washed with ether (2 × 20 ml.), acidified with 6 N hydrochloric acid and extracted with ethyl acetate (4 × 50 ml.). The combined extracts were washed with water (2 × 50 ml.) and dried with anhydrous $Na_2SO_4$. Evaporation of the solvent gave an oily residue, which was chromatographed on a silica gel column (Wako-gel, C-200, 25 g.) by eluting with chloroform-methanol (0-3%). The fractions which contained the desired product were collected (by tlc monitoring) and evaporation of the solvent gave an oily residue which was triturated with n-hexane-ether to afford 530 mg. (42%) of 2 as an amorphous powder m.p. 100° C. (decomp.).

ir: $\eta_{max}^{KBr}$ 1780, 1760, 1700, 1240, 1150 cm$^{-1}$.

uv: $\lambda_{max}^{Buff(pH7)}$ 267 nm ($\epsilon$, 8700).

Anal. Calc'd. for $C_{25}H_{29}N_7O_9S_2.(C_2H_5)_2O$: C, 49.07; H, 5.54; N, 13.81; S, 8.81. Found: C, 49.41; H, 5.34; N, 12.57; S, 8.24.

7-[(2-Aminomethyl-4-hydroxyphenyl)acetamido]-3-(1-carboxymethyltetrazol-5-ylthiomethyl)-3-cephem-4-carboxylic acid (3)

Trifluoroacetic acid (2 ml.) was added to the N-BOC protected cephalosporin 2 (470 mg., 0.74 mmol.) at 0° C. and the mixture was stirred for 30 minutes at 10°–15° C. The trifluoroacetate of 3 given by the addition of anhydrous ether (50 ml.) was collected by filtration and dissolved in a mixture of acetonitrile (10 ml.) - water (10 ml.). To the solution was added conc. ammonium hydroxide to adjust to pH 6 and the mixture was diluted with acetonitrile (100 ml.) to deposit the precipitate 3 which was collected by filtration, washed with acetonitrile (10 ml.) and dried in vacuo. Yield 270 mg. (68%). m.p. 150°–160° C. (decomp.).

The addition of 1.55 ml. of 1.55 ml. of Water for Injection, U.S.P./vial gives 2 ml. of a pH 7.7 solution containing 250 mgm./ml. on an activity basis of BL-S786 activity as the free-acid.

Use before 6 hours at room temperature (23° C.) or 24 hours under refrigeration (4°–6° C.).

Another example of the mixture is the following.

Parenteral BL-S786 Free-Acid: L-Lysine Mixture
(Label Claim is 250 mg. of Activity
as BL-S786 Free Acid/ml.)

Formula

| | |
|---|---|
| Sterile, Pyrogen-Free BL-S786 Free-Acid, (200 mesh;potency = 1000-1050 mcg./mg., Klett Color = 35) | *[1]0.25 Gram |
| Sterile, Pyrogen-Free L-Lysine, (200 mesh) | *[2]0.0875 Gram |
| Fill | *[3]0.3375 Grams |

*[1]Assuming a potency of 1000 mcg./mg.
*[2]This represents 35% of the weight of the BL-S786 free acid, assuming a potency of 1000 mcg./mg. This weight may be held constant with a potency range of 1000–1050 mcg./mg. for the BL-S786 free-acid.
*[3]This weight may also be increased by adding increments based on the following factors.
1) Overbatch required for shelf life (stability).
2) Overfill required for vial, syringe and needle holdup.
3) Machine fill variability.

MANUFACTURING INSTRUCTIONS (1.) Double check all weights before loading.
(2.) Use sterile, lint-free procedures.
(3.) Spray area with peracetic acid before doing any sterile work.
(4.) Relative humidity for all operations should be 25% or less.
  (a) Aseptically add the 200 mesh, sterile, pyrogen-free BL-S786 free-acid and L-Lysine to a suitable sterile blender. Seal the blender.
  (b) Rotate blender for 2 hours at 5 rpm.
  (c) Pass the blended mixture through a suitable sterile mill containing the equivalent of a 60-mesh screen.
  (d) Place batch into a sterile blender and blend for 1 hour at 5 rpm.
  (e) Drop the sterile drums to be transferred to sterile 20 liter bottles by the sampling operator.
  (f) Fill.

The following mixtures are prepared in similar fashion.

FORMULA

Each 8.5 cc. vial contains the equivalent of 250,000 units of BL-S786 free-acid activity.

| | |
|---|---|
| BL-S786 free-acid (1044 mcg./mg.) | = 0.240 grams |
| L-Lysine | = 0.084 grams |
| | 0.324 grams/vial |

The addition of 0.77 ml. of Water for Injection, U.S.P. gives 1 ml. of a pH 7.7, 250,000 units/ml. solution as BL-S786 free-acid activity.

FORMULA

Each 50 cc. vial contains the equivalent of 5 grams (5 million units) of BL-S786 free-acid activity.

| | |
|---|---|
| BL-S786 free-acid (1044 mcg./mg.) | = 4.80 grams |
| L-Lysine | = 1.68 grams |
| | 6.48 grams/vial |

Using Water for Injection, U.S.P., the following pH 7.7 solutions are obtained.

| Concentration in mg/ml of BL-S786 Activity | Volume of Water to be added to 50 cc vial | Volume of Solution |
|---|---|---|
| 250 | 15.5 ml. | 20.0 ml. |
| 300 | 12.0 ml. | 16.6 ml. |
| 350 | 9.8 ml. | 14.3 ml. |
| 400 | 8.0 ml. | 12.5 ml. |

The solutions should be used within 6 hours at room temperature (23° C.) or 24 hours at refrigeration (4° C.). The 400 mg./ml. solution at 4° C. may form a gelatinous precipitate. The precipitate dissolves completely upon warming to room temperature.

Preparation of Sterile, Lyophilized Parenteral-
Grade BL-S786: L-Lysine Salt
(Label Claim is 250 mg. of BL-S786 Activity/ml.)

Formula

| | |
|---|---|
| BL-S786 free-acid (potency = 1000–1050 mcg./ml.; Klett Color = 20-30) | *[1]0.25 gram |
| Parenteral grade L-Lysine | *[2]0.0875 gram |
| Water for Injection, U.S.P. | qs to 1 ml. |

*[1]Label claim is 0.25 gram BL-S786 activity as the free-acid. The amount of BL-S786 free-acid required is calculated as follows:

$$\frac{0.25 \text{ gm} \times 1000}{\text{Potency of BSL-S786 free acid in mcg/mg}} = \text{Weight in grams of BL-S786 free-acid.}$$

This weight may also be increased by adding increments based on the following factors; 1) Overbatch required for shelf life (stability) 2) Overfill required for vial and needle holdup 3) Machine fill variability
*[2]This represents 35% of the weight of the BL-S786 free-acid, assuming a potency of 1000 mcg./mg.

MANUFACTURING INSTRUCTIONS (1.) Slurry 100 grams (100 million units) of pyrogen-free BL-S786 free-acid (1000 mcg./mg., Klett Color: 20–30) in 250 ml. of Water for Injection, U.S.P. at 20°–24° C.

(2.) Add with rapid stirring, over a 5 minute interval, 35 grams of pyrogen-free L-Lysine. A pH 7.4–8.0 solution or near solution is obtained. Add Water for Injection, U.S.P. to a final volume of 400 ml. (A 10 gram activated carbon 0.5 hour slurry in this step is optimal).

(3.) Pass the solution through suitable filters to remove particles and bacteria.

(4.) Using sterile technique, fill the required volume of sterile, pyrogen-free solution of step 3 into sterile glass vials.

Steps 2 to 4 inclusive should be completed within 3 hours. Freeze immediately.

(5.) Under sterile conditions lyophilize for 48 hours. Maintaining vacuum, continue at 50° C. for 24 hours. Cool to 22°–25° C. and release vacuum.

(6.) Suitable stopper and cap.

PROPERTIES OF LYOPHILIZED BL-S786: L-LYSINE SALT (1.) Bio assay: 700–745 mcg./mg. (theory = 742 mcg./mg.).
(2.) NMR; IR: Consistent for structure (1.5–1.7 mole of L-Lysine per 1 mole of BL-S786).
(3.) % Water, KF: 1.4–3.0.
(4.) pH of 250 mg./ml. of BL-S786 activity in reconstituted solution: 7.5.
(5.) Stability of above solution: Less than 10% lost at 23° C. for 5–8 hours. At 25 mg./ml. of BL-S786 activity, less than 10% lost for 24 hours at 23° C.
(6.) Klett Color (1.4% in 1% pH 7.0 phosphate buffer using a #42 blue filter): 22–50.

(7.) Solid Stability: Less than 10% loss for 1 month at 45° C.

We claim:

1. A compound having the formula

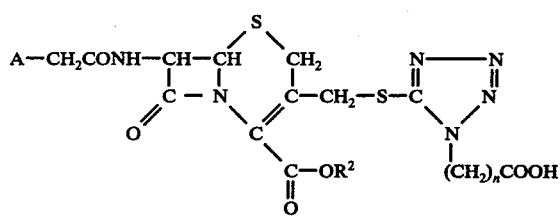

wherein A represents

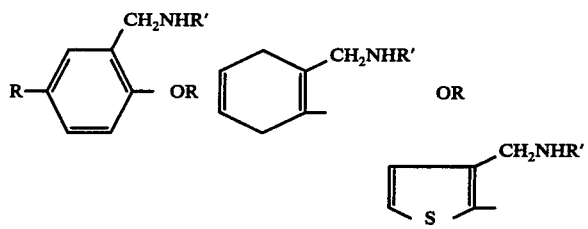

wherein R is hydrogen, hydroxy or methoxy; R' is hydrogen or methyl; n is one, two or three; and $R^2$ is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl.

2. A nontoxic pharmaceutically acceptable salt of a compound of claim 1.

3. A compound having the formula

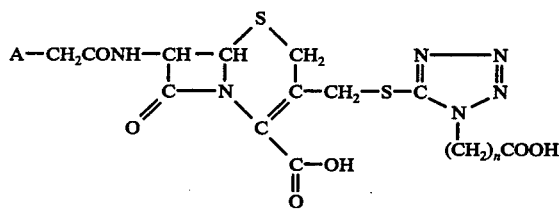

wherein A represents

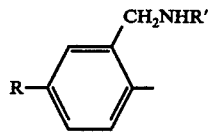

wherein R is hydrogen, hydroxy or methoxy or

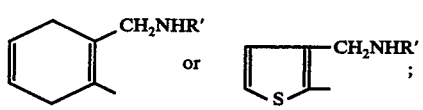

R' is hydrogen or methyl; and n is one, two or three.

4. A nontoxic pharmaceutically acceptable salt of a compound of claim 3.

5. A compound having the formula

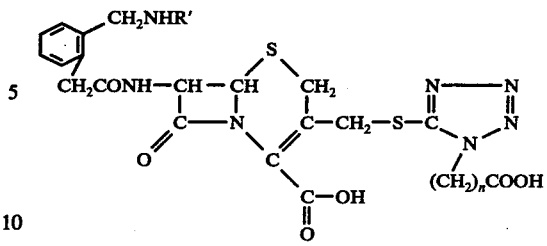

wherein R' is hydrogen or methyl and n is one, two or three.

6. A nontoxic, pharmaceutically acceptable salt of a compound of claim 5.

7. The compound of claim 5 having the formula

[structure with CH₂NH₂, $(CH_2)_n$COOH]

8. A nontoxic, pharmaceutically acceptable salt of the compound of claim 7.

9. The compound of claim 5 having the formula

[structure with CH₂NH₂, CH₂CH₂COOH]

10. The compound of claim 5 having the formula

[structure with CH₂NH₂, CH₂CH₂CH₂COOH]

11. The compound of claim 5 having the formula

[structure with CH₂NH CH₃, CH₂COOH]

12. The compound of claim 5 having the formula

13. The compound of claim 5 having the formula
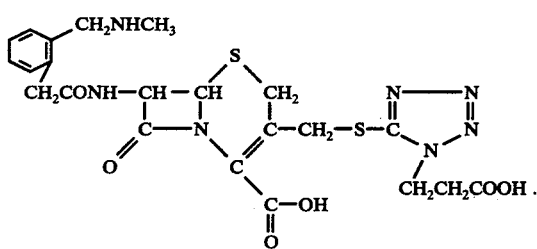
14. The compound of claim 1 having the formula
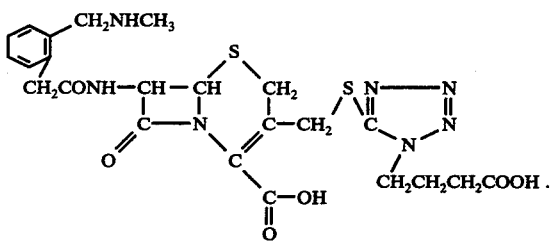
15. The compound of claim 1 having the formula
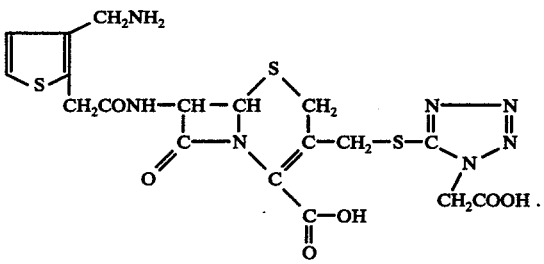
16. The compound of claim 1 having the formula
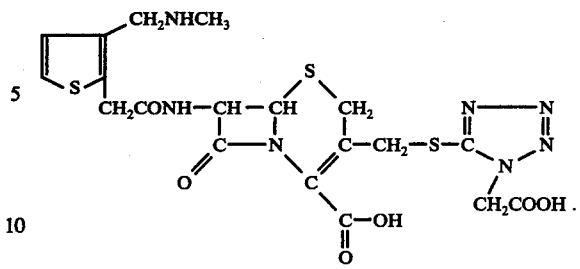
17. A compound having the formula:
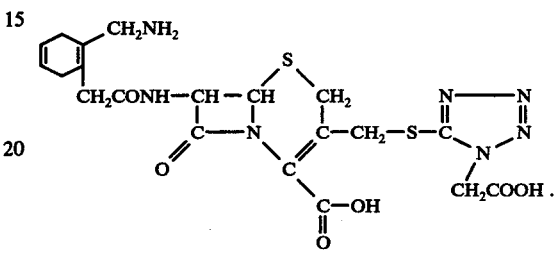
wherein $n$ is one, two or three.
* * * * *

UNITED STATES PATENT AND TRADEMARK OFFICE
CERTIFICATE OF CORRECTION

PATENT NO. : 4,100,346
DATED : July 11, 1978
INVENTOR(S) : William J. Gottstein, Murray A. Kaplan and Alphonse P. Granatek It is certified that error appears in the above-identified patent and that said Letters Patent are hereby corrected as shown below:

In claim 7 structural formula should read

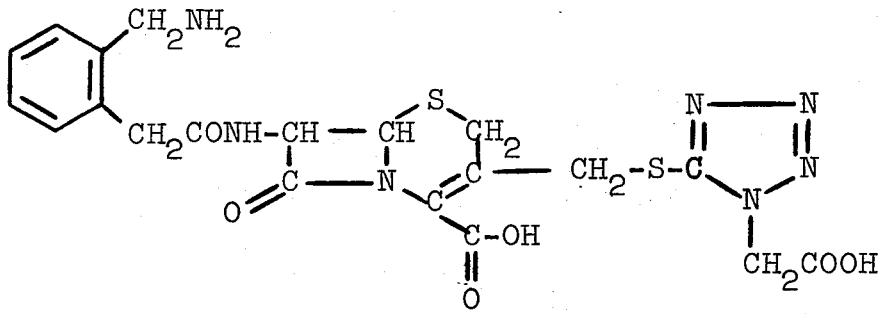

Signed and Sealed this

Sixth Day of February 1979

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,100,346
DATED : July 11, 1978
INVENTOR(S) : William J. Gottstein, Murray A. Kaplan and Alphonse P. Granatek It is certified that error appears in the above-identified patent and that said Letters Patent are hereby corrected as shown below:

In claim 7 structural formula should read

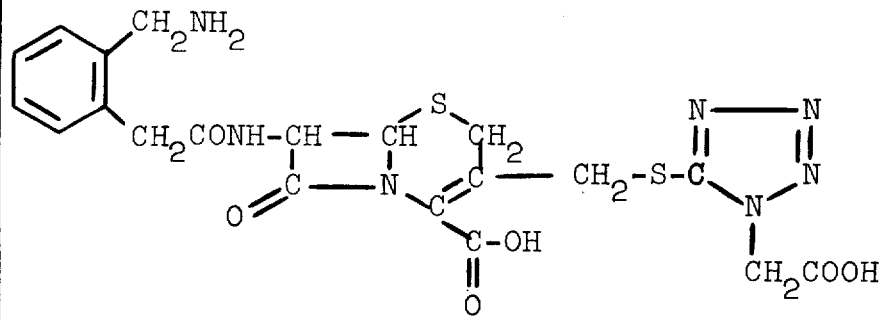

Signed and Sealed this

Sixth Day of February 1979

[SEAL]

Attest:

RUTH C. MASON
Attesting Officer

DONALD W. BANNER
Commissioner of Patents and Trademarks